United States Patent
Striker et al.

(10) Patent No.: US 11,820,753 B2
(45) Date of Patent: Nov. 21, 2023

(54) INHIBITORS OF BACTERIAL PASTA KINASES

(71) Applicant: Wisconsin Alumni Research Foundation, Madison, WI (US)

(72) Inventors: Robert Todd Striker, Madison, WI (US); Nathan Joseph Wlodarchak, Madison, WI (US); John Bruce Feltenberger, Madison, WI (US); Jennifer Golden, Waunakee, WI (US)

(73) Assignees: Wisconsin Alumni Research Foundation, Madison, WI (US); U.S. Dept. of Veterans Affairs, Washington, DC (US)

( * ) Notice: Subject to any disclaimer, the term of this patent is extended or adjusted under 35 U.S.C. 154(b) by 113 days.

(21) Appl. No.: 17/172,314

(22) Filed: Feb. 10, 2021

(65) Prior Publication Data
US 2022/0251062 A1    Aug. 11, 2022
US 2023/0060122 A9    Feb. 23, 2023

Related U.S. Application Data

(60) Provisional application No. 62/972,349, filed on Feb. 10, 2020.

(51) Int. Cl.
| | |
|---|---|
| C07D 401/04 | (2006.01) |
| C07D 239/42 | (2006.01) |
| C07D 417/04 | (2006.01) |
| C07D 277/28 | (2006.01) |
| A61K 31/506 | (2006.01) |
| A61K 45/06 | (2006.01) |
| A61K 31/496 | (2006.01) |
| A61P 31/06 | (2006.01) |

(52) U.S. Cl.
CPC .......... *C07D 401/04* (2013.01); *A61K 31/496* (2013.01); *A61K 31/506* (2013.01); *A61K 45/06* (2013.01); *A61P 31/06* (2018.01); *C07D 239/42* (2013.01); *C07D 277/28* (2013.01); *C07D 417/04* (2013.01)

(58) Field of Classification Search
CPC .. C07D 401/04; C07D 239/42; C07D 277/28; C07D 417/04; A61P 31/06; A61K 31/496; A61K 31/506; A61K 45/06
USPC .................................................... 514/252.18
See application file for complete search history.

(56) References Cited

U.S. PATENT DOCUMENTS 4,876,252 A * 10/1989 Torley .................. C07D 401/04
544/122

* cited by examiner

*Primary Examiner* — Kristin A Vajda
(74) *Attorney, Agent, or Firm* — Boyle Fredrickson S.C.

(57) ABSTRACT

Biochemically active PASTA kinase inhibitors which exploit subtle structural differences between human kinases and bacterial PASTA kinases to improve specificity and inhibitor activity. The disclosed kinase inhibitors have the general formula:

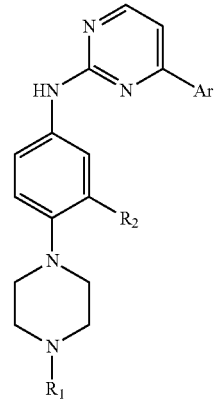

wherein:
$R_1$=Me, Et, n-Pr, —$CH_2CH_2OH$, —$CH_2CH_2OP(O)(OH)_2$, —$CH_2CH_2NMe_2$;
$R_2$=H, Me, Et, o-Pr, i-Pr, $CF_3$, Cl, OMe;
$R_3$=H, Me, NHMe, NHBn, Cl, $NO_2$OMe, F, CN; and
Ar=

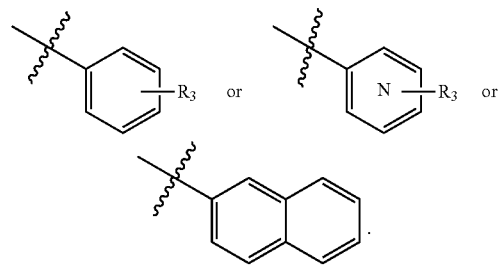

14 Claims, 21 Drawing Sheets

| Structure | NAME | cLogP | Docking Energy (kcal/mol) | PknB IC50 (uM) | PknB Kd (nM) | Cdk2 IC50 (uM) | Mtb MIC NO mero (uM) | Zebrafish Toxicity (% survival 5dpf 25uM) |
|---|---|---|---|---|---|---|---|---|
| CN(CC1CCN1C(C(C(F)(F)F)=C2)=CC=C2NC3=NC=CC(C4=C5N(N=CC=C5)N=C4)=N3 | GW779439x | | -10.32 | 0.69±0.19 | 12 | 1.4±0.82 | 100 (100, 100) ±0 | 0 (0, 0) ±0 |
| CN(CC1)CCN1C(C(C(F)(F)F)=C2)=CC=C2NC3=NC=CC(C4=CC=CN=C4)=N3 | UW011 | | -9.35 | 4.5±2.8 | 63 | 9.3±2.8 | >100 | 33 (33, 0) ±11 |
| CN(CC1)CCN1C(C(C(F)(F)F)=C2)=CC=C2NC3=NC=CC(C4=CC=NC=C4)=N3 | UW012 | | -9.44 | 2.4±0.39 | 78 | 4.6±1.5 | >100 | 0 (0, 0) ±0 |
| CN(CC1)CCN1C(C(C(F)(F)F)=C2)=CC=C2NC3=NC=CC(C4=CC=NC(NCC5=CC=CC= | UW015 | | -11 | 8.9±1.1 | 1700 | 7.3±0.92 | >100 | 0 (0, 0) ±15 |
| CN(CC1)CCN1C(C(C(F)(F)F)=C2)=CC=C2NC3=NC=CC(C4=CC=NC(Cl)=C4)=N3 | UW031 | | -9.98 | 1.4±0.30 | 0.21 | 7.2±0.20 | 50 (50, 50) ±0 | 11.1 (56, 0) ±17 |
| CN1CCN(CC1)c2c(cc(cc2)Nc3nccc(n3)c4ccccc4)C(F)(F)F | UW042 | 4.37 | -9.59 | 9.7±3.5 | 1600 | >40 | 25 (25, 25) ±0 | 0 (22, 0) ±7.4 |
| CN1CCN(CC1)c2c(cc(cc2)Nc3nccc(n3)c4cccc(cc4)[N+](=O)[O-])C(F)(F)F | UW048 | 2.52 | -11.14 | | 380 | | 25 (25, 25) ±0 | 56 |
| CN1CCN(CC1)c2c(cc(cc2)Nc3nccc(n3)c4cccc(cc4)Cl)C(F)(F)F | UW049 | | -9.75 | 8.1±1.3 | 1700 | >40 | 25 (13, 25) ±4.2 | 0 (0, 0) ±0 |
| CN1CCN(CC1)c2c(cc(cc2)Nc3nccc(n3)c4ccccc(c4)Cl)C(F)(F)F | UW051 | | -10.14 | 4.0±0.44 | | >40 | 13 (13, 25) ±4.2 | 0 (0, 0) ±0 |
| CN1CCN(CC1)c2c(cc(cc2)Nc3nccc(n3)c4ccccc(cc4)[N+](=O)[O-])C(F)(F)F | UW052 | | -10.74 | 1.2±0.32 | 45 | >40 | 50 (25, 50) ±8.3 | 0 (0, 0) ±0 |
| CN1CCN(CC1)c2c(cc(cc2)Nc3nccc(n3)c4cccc(c4)OC)C(F)(F)F | UW055 | 4.3 | -10.36 | 6.6±0.33 | 790 | 10±2 | 25 (25, 25) ±0 | 0 (0, 0) ±0 |
| CN1CCN(CC1)c2c(cc(cc2)Nc3nccc(n3)c4cc5ccccc5cc4)C(F)(F)F | UW059 | | -10.44 | 3.4±0.16 | 320 | >40 | 13 (13, 13) ±0 | 0 (0, 0) ±0 |
| CN(CC1)CCN1C(C(C(F)(F)F)=C2)=CC=C2NC3=NC=CC(C4=CC=NC(NC)=C4)=N3 | UW107 | | -9.94 | | 1200 | | 25 | 0 (0, 0) ±0 |
| CN(CC1)CCN1C(C(C(F)(F)F)=C2)=CC=C2NC3=NC=CC(C4=CC=C(C)C=C4)=N3 | UW108 | | -9.65 | | 43 | | 100 | 0 (0, 0) ±0 |
| CN(CC1)CCN1C(C(C(F)(F)F)=C2)=CC=C2NC3=NC=CC(C4=CC=C(F)C=C4)=N3 | UW109 | 4.47 | -9.65 | | 1100 | | 25 | 0 (0, 0) ±0 |
| CN(CC1)CCN1C(C(C(F)(F)F)=C2)=CC=C2NC3=NC=CC(C4=CC(F)=CC=C4)=N3 | UW110 | | -9.61 | | 800 | | 25 | 0 (0, 0) ±0 |
| CN(CC1)CCN1C(C(C(F)(F)F)=C2)=CC=C2NC3=NC=CC(C4=CC=CC(C#N)=C4)=N3 | UW111 | | -10.57 | | 31 | | >100 | 0 |
| CN(CC1)CCN1C(C(C(F)(F)F)=C2)=CC=C2NC3=NC=CC(C4=CC=C(C#N)C=C4)=N3 | UW112 | | -10.4 | | 240 | | 50 | 0 |
| CN(CC1)CCN1C(C(C(F)(F)F)=C2)=CC=C2NC3=NC=CC(C4=CC=CC=C4Cl)=N3 | UW113 | | -9.64 | | 2600 | | 50 | 0 |
| CN(CC1)CCN1C(C(C(F)(F)F)=C2)=CC=C2NC3=NC=CC(C4=CC=CC(Cl)=C4)=N3 | UW114 | 4.71 | -9.99 | | 430 | | 25 | 0 |

FIG. 4a

| Structure (SMILES) | ID | Value1 | Value2 | Value3 | Value4 | Value5 | Value6 |
|---|---|---|---|---|---|---|---|
| C(NH+)1CCN(C2=CC=C(NC3=NC=C(C4=CC(Cl)=NC=C4)S3)C=C2C(F)(F)F)CC1 | UW115 | -9.06 | | | | | 0 |
| C(NH+)1CCN(C2=CC=C(NC3=NC=C(C4=CC=CC=C4)S3)C=C2C(F)(F)F)CC1 | UW116 | -8.93 | >20 | | | | 0 |
| C(NH+)1CCN(C2=CC=C(NC3=NC=C(C4=CC(C#N)=CC=C4)S3)C=C2C(F)(F)F)CC1 | UW117 | -9.93 | | | | | 0 |
| C(NH+)1CCN(C2=CC=C(NC3=NC=C(C4=CC([N+]([O-])=O)=CC=C4)S3)C=C2C(F)(F)F | UW118 | -10.4 | | | | | 0 |
| C(NH+)1CCN(C2=CC=C(NC3=NC=C(C4=CC=CC=C5)=C5C=C4)S3)C=C2C(F)(F)F | UW119 | -9.88 | | | | | 0 |
| CN(C)CCN(CC1)CCN1C(C(F)(F)F)=C2)=CC=C2NC3=NC=CC(C4=CC=CC=C4)=N3 | UW120 | 4.07 | 7.9±0.4 | | | 50 | 0 |
| CN(C)CCN(CC1)CCN1C(C(F)(F)F)=C2)=CC=C2NC3=NC=CC(C4=CC=CC([N+])([O-])) | UW121 | 1.11 | 5.6±0.2 | | | 50 | 0 |
| CN(C)CCN(CC1)CCN1C(C(F)(F)F)=C2)=CC=C2NC3=NC=CC(C4=CC=CC(OC)=C4 | UW122 | 4.03 | | | | | 0 |
| CN(C)CCN(CC1)CCN1C(C(F)(F)F)=C2)=CC=C2NC3=NC=CC(C4=CC(F)C=C4)= | UW123 | 4.17 | 6.8±0.6 | | | 25 | 0 |
| CN(C)CCN(CC1)CCN1C(C(F)(F)F)=C2)=CC=C2NC3=NC=CC(C4=CC=CC(C)=C4)= | UW124 | 4.42 | | | | | 0 |
| CC(OC(N(CC1)CCN1C(C(F)(F)F)=C2)=CC=C2NC3=NC=CC(C4=CC(OC)=CC=C4)= | UW130 | | >20 | | | >50 | 0 |
| CC(OC(N(CC1)CCN1C(C(F)(F)F)=C2)=CC=C2NC3=NC=CC(C4=CC(OC)=CC=C4)= | UW131 | | >20 | | | >50 | 0 |
| FC(C=C1)=CC=C1C2=NC(NC3=CC=C(N4CCN(C(OC(C)C)=O)CC4)C(C(F)(F)F)=C | UW132 | | >20 | | | >50 | 0 |
| FC(F)(F)C1=CC(NC2=NC=CC(C3=CC(OC)=CC=C3)=N2)=CC=C1N4CCNCC4 | UW133 | | 4.5±1.4 | | | >50 | 0 |
| FC(F)(F)C1=CC(NC2=NC=CC(C3=CC(OC)=CC=C3)=N2)=CC=C1N4CCNCC4 | UW134 | | 3.7±0.2 | | | >50 | 0 |
| FC(C=C1)=CC=C1C2=NC3=CC=C(N4CCNCC4)C(C(F)(F)F)=C3)=NC=C2 | UW135 | | 4.8±1.6 | | | >50 | 0 |
| OCCN(CC1)CCN1C2=C(C(F)(F)F)C=C(NC3=NC(C4=CC=CC=C4)=CC=N3)C=C2 | UW136 | | | | | | |
| OCCN(CC1)CCN1C2=C(C(F)(F)F)C=C(NC3=NC(C4=CC=C(F)C=C4)=CC=N3)C=C2 | UW137 | | | | | | |
| OCCN(CC1)CCN1C2=C(C(F)(F)F)C=C(NC3=NC(C4=CC(OC)=CC=C4)=CC=N3)C=C2 | UW138 | | | | | | |
| OCCN(CC1)CCN1C(C(F)(F)F)=C2)=CC=C2NC3=NC=CC(C4=CC(C)=CC=C4)=N3 | UW139 | | | | | | |
| OCCN(CC1)CCN1C(C(F)(F)F)=C2)=CC=C2NC3=NC=CC(C4=CC=CC([N+])([O-])=O)C | UW140 | | | | | | |

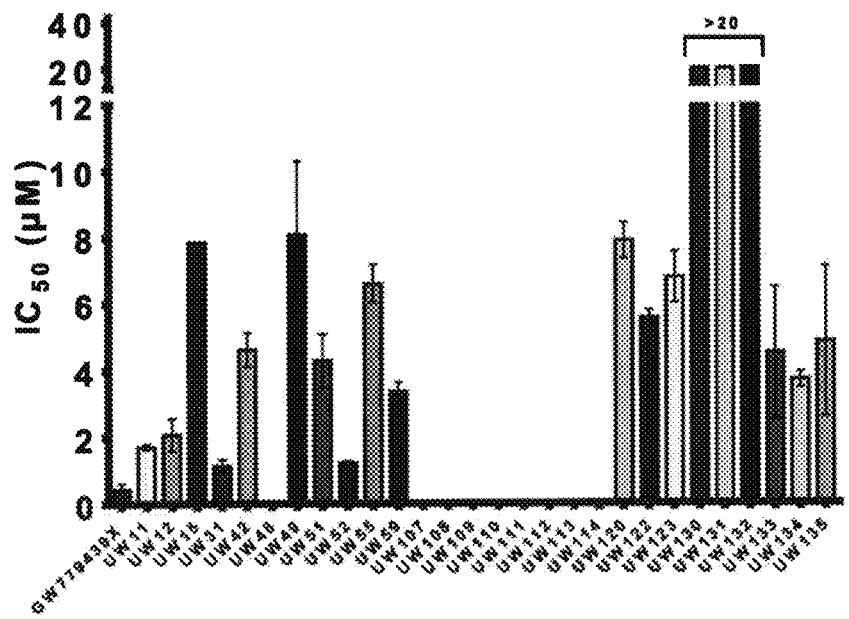
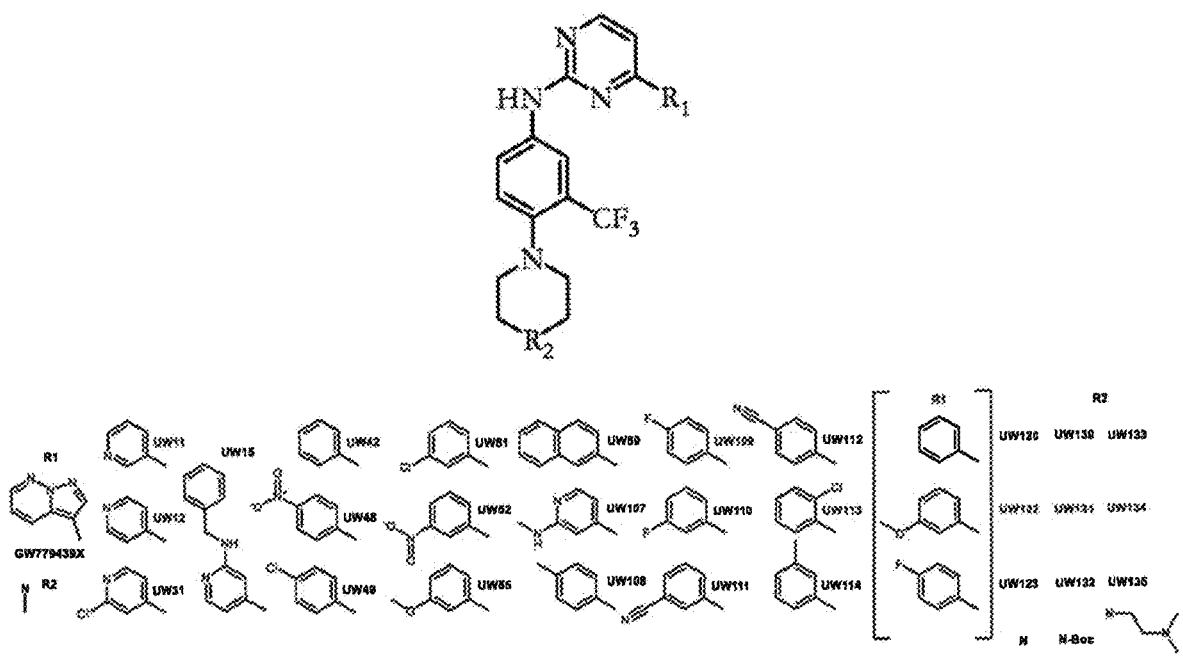
FIG. 6

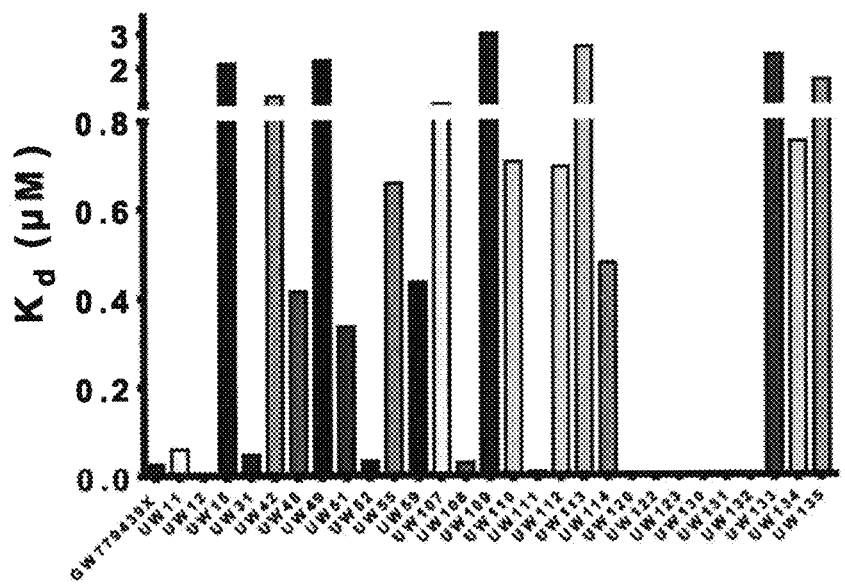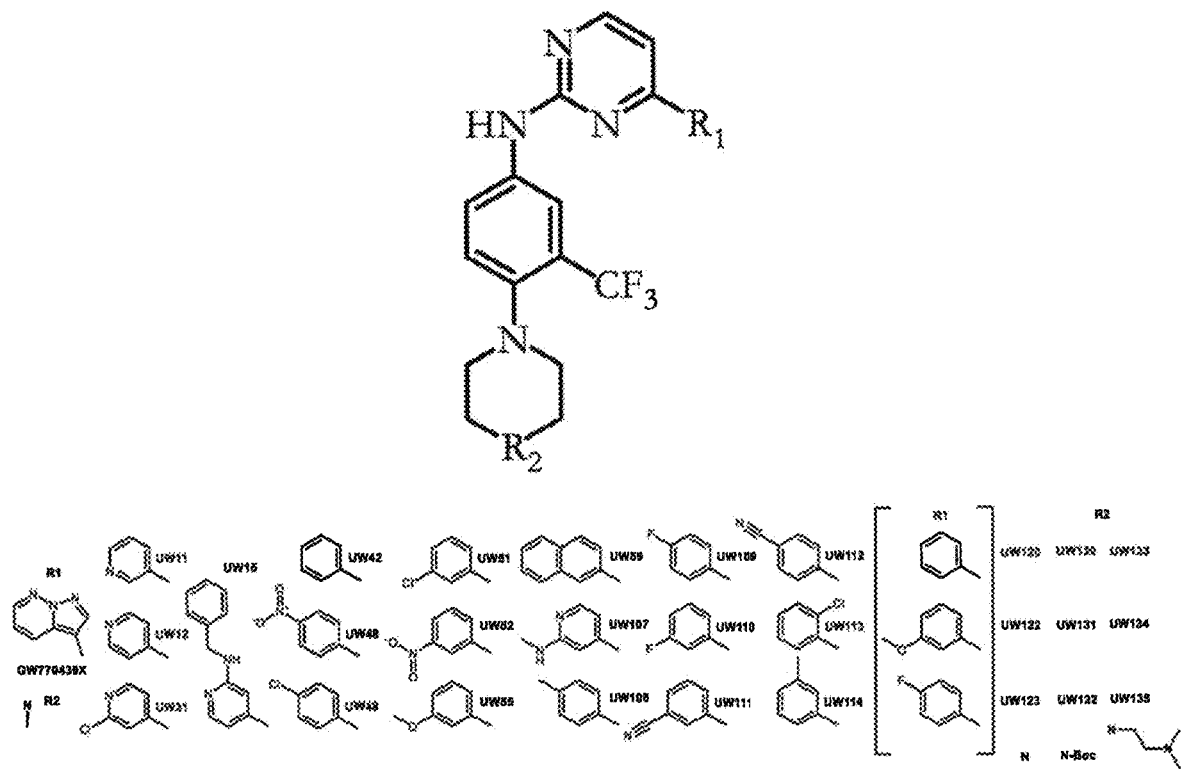
FIG. 7

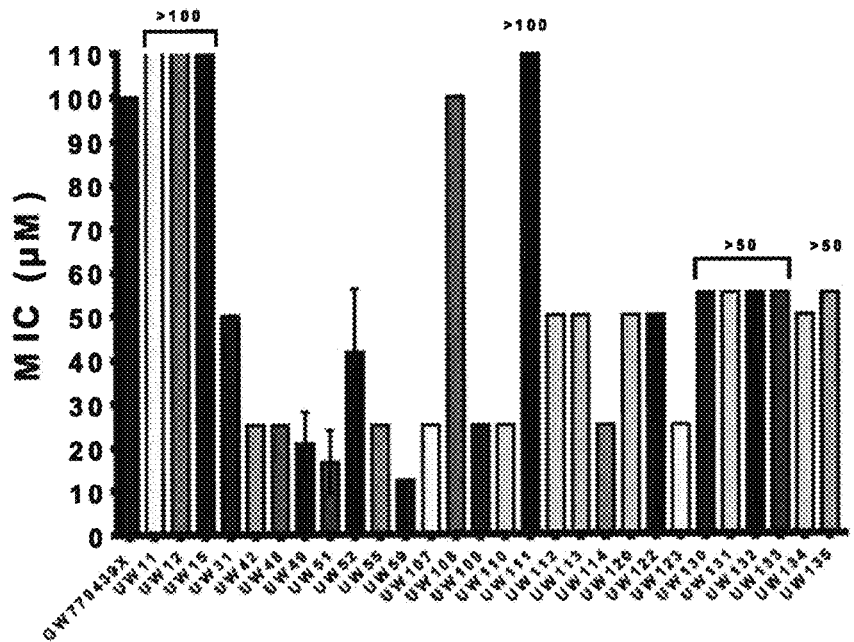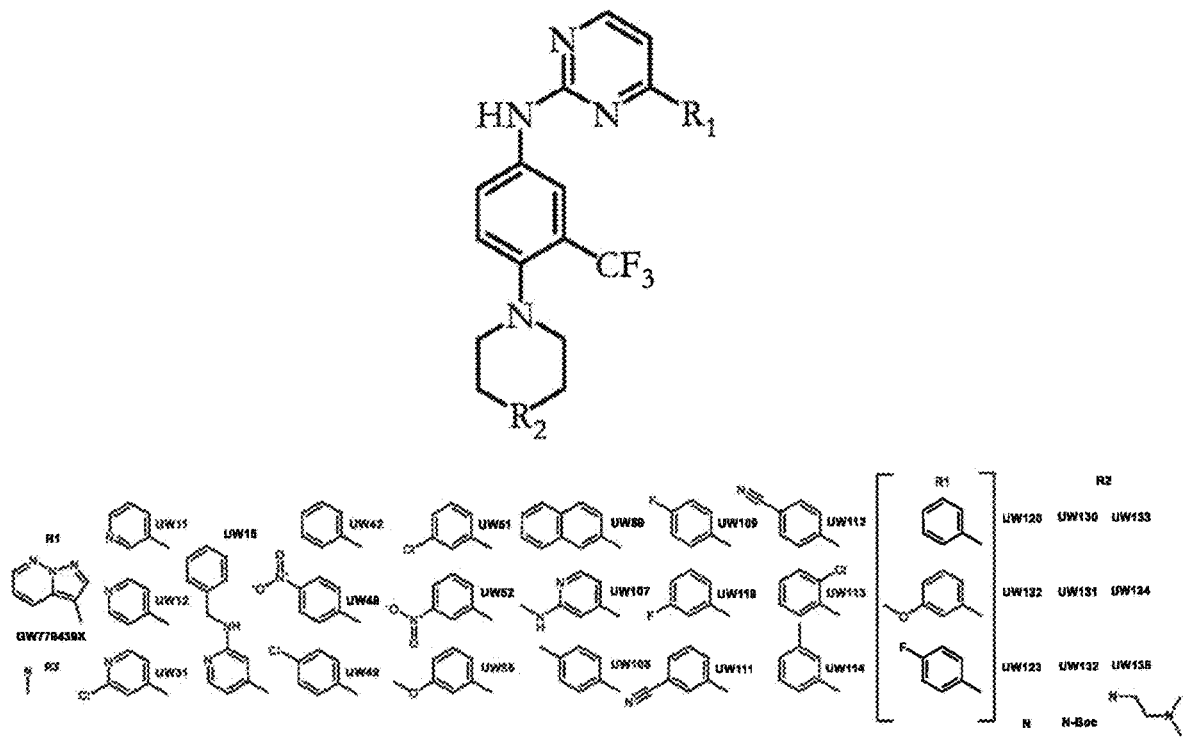
FIG. 8

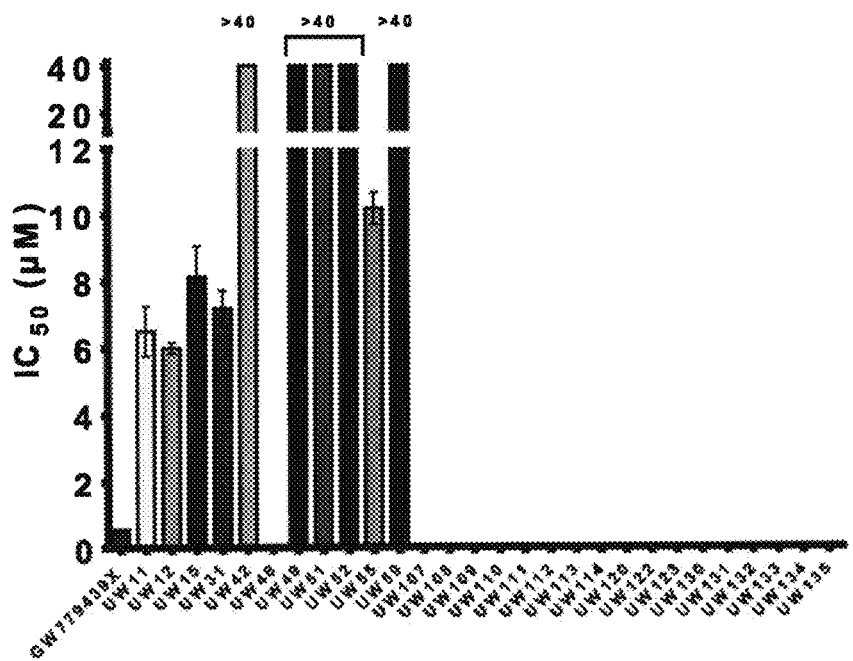
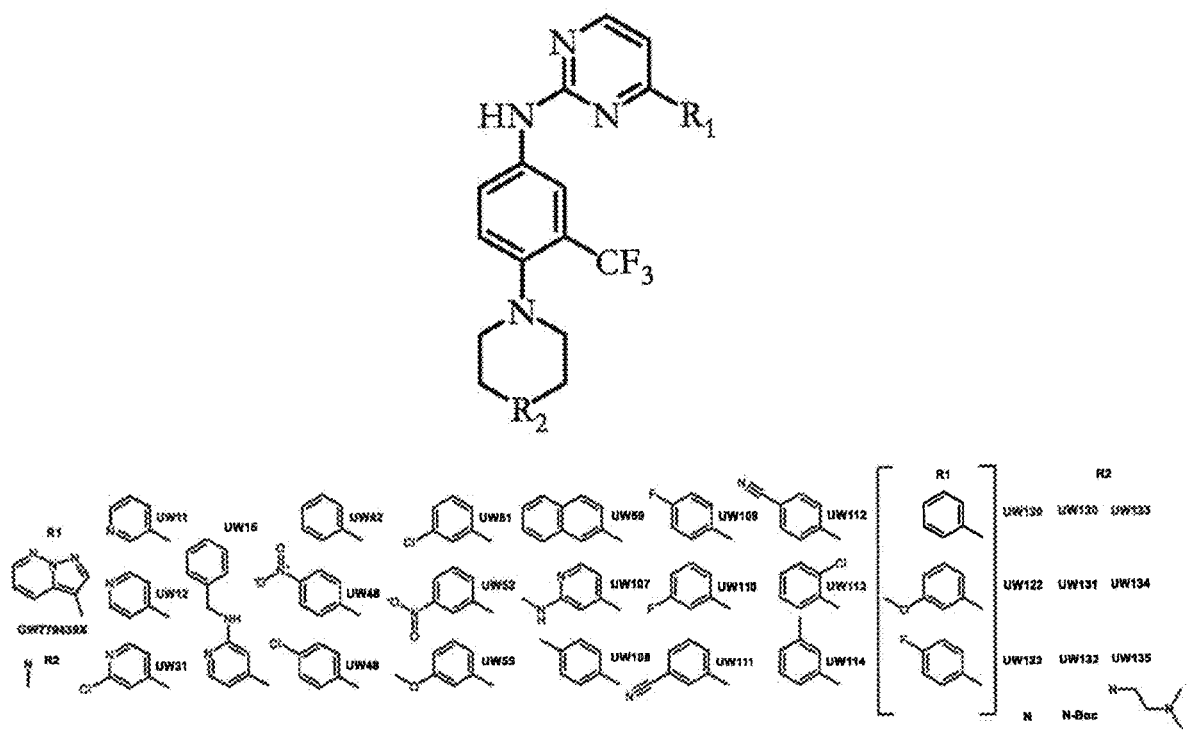
FIG. 9

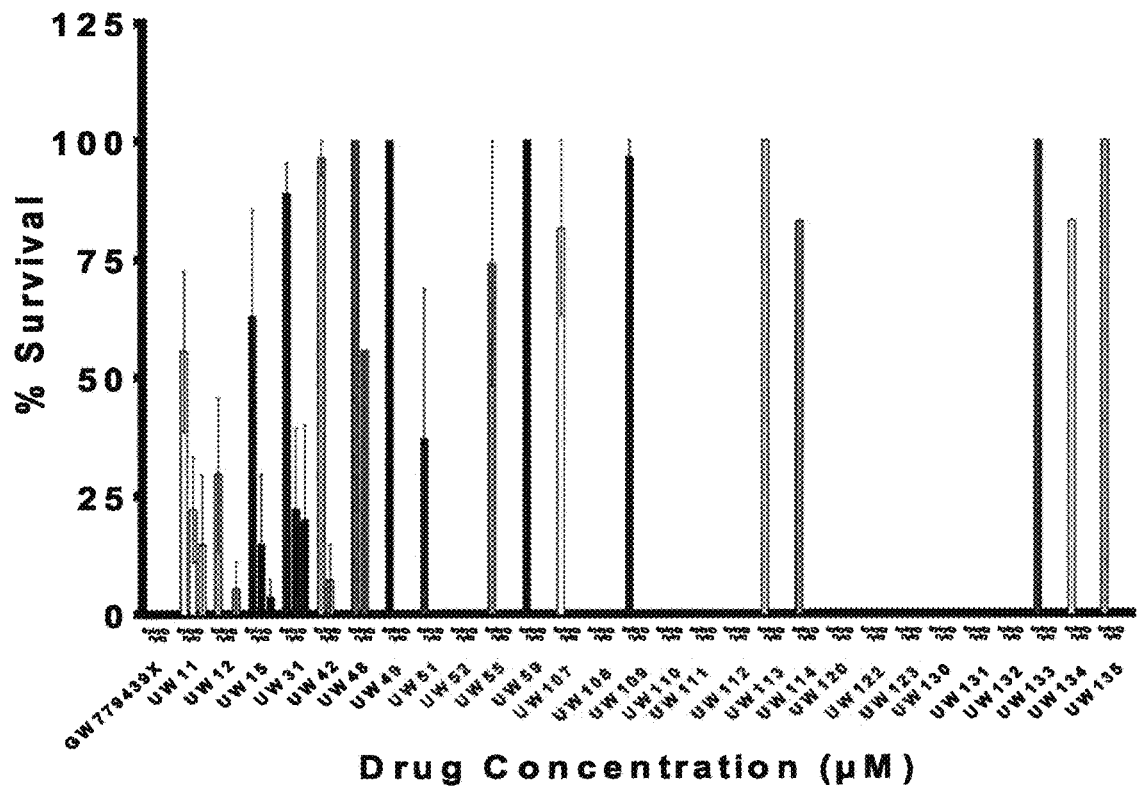
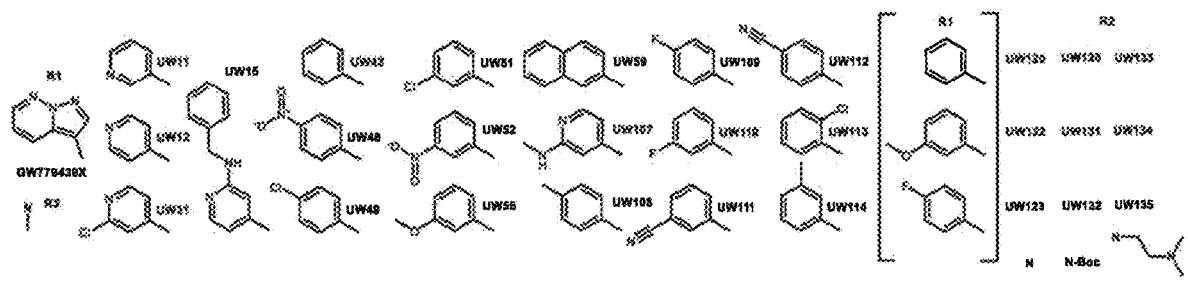
FIG. 10

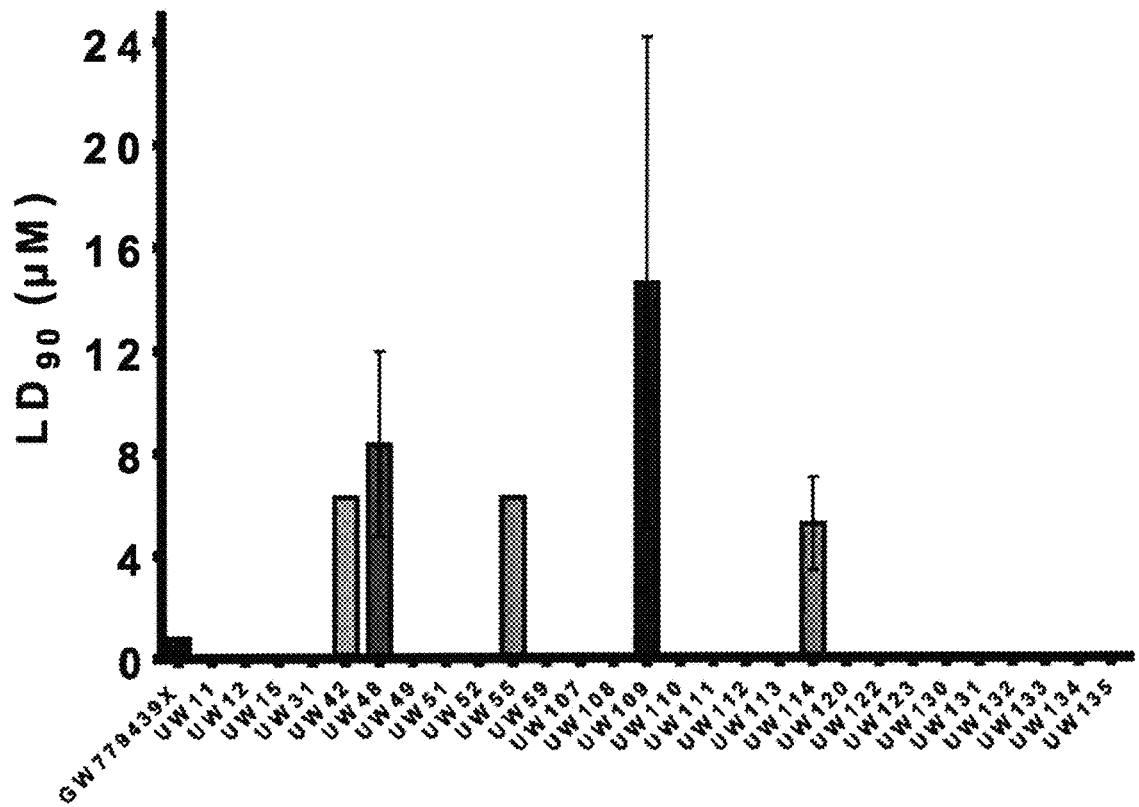
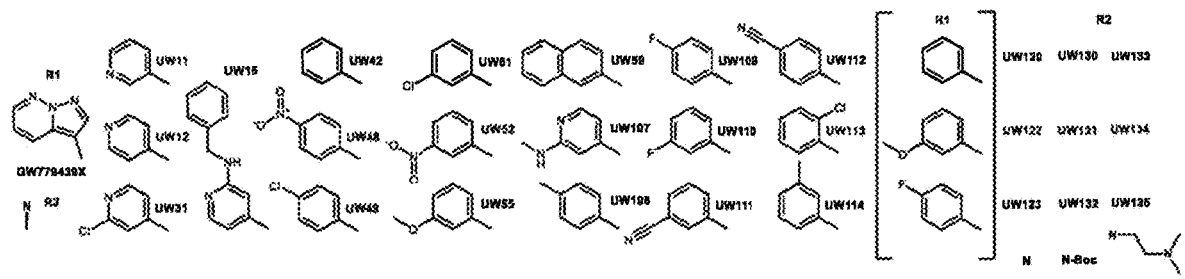
FIG. 11

INHIBITORS OF BACTERIAL PASTA KINASES

CROSS-REFERENCE TO RELATED APPLICATIONS

This application claims the benefit of U.S. Provisional Application No. 62/972,349, filed Feb. 10, 2020, and hereby incorporated by reference.

STATEMENT REGARDING FEDERALLY FUNDED RESEARCH AND DEVELOPMENT

This invention was made with government support under Grant No. 1 I01 BX004089-01 awarded by the Veterans Administration. The government has certain rights in the invention.

FIELD OF THE INVENTION

This invention relates generally to the inhibition of protein kinases for therapeutic purposes. More particularly, the present invention is directed to Penicillin-binding And Serine/Threonine Associated (PASTA) kinase inhibitors which exploit subtle structural differences between human kinases and bacterial PASTA kinases to improve specificity and activity.

BACKGROUND OF THE INVENTION

Antibiotic resistant pathogens are a growing worldwide threat. If left unchecked, deaths due to antibiotic resistant infections could eclipse current cancer mortality rates. Unfortunately, resistance is easily acquired because current antibiotics target a narrow range of bacterial processes, primarily cell wall growth and remodeling, protein biosynthesis, and bacteria-specific metabolism. During the antibiotic "golden age," the standard dogma was to avoid bacterial targets with any homology to human proteins. This severely limited exploration of many targets. Notably, signal transduction cascades were either not discovered or not explored. Since that time, most pharmaceutical companies abandoned their work on antibiotics due to perceived lack of need and low financial returns. Concurrently, antibiotic abuse in agriculture and medicine combined with steady bacterial evolution and stagnant drug development rapidly led to an antibiotic resistance crisis. This situation is especially critical for bacterial infections that already had limited treatment options.

Gram positive pathogens such as mycobacteria and *Staphylococcus aureus*, are not only intrinsically antibiotic resistant, but multi-drug resistant strains are rapidly spreading. Two billion people are currently infected with *Mycobacterium tuberculosis*, and an increasing proportion are multi-drug resistant and extra-drug resistant. Methicillin resistant *Staphylococcus aureus* (MRSA) is a massive burden in healthcare, and vancomycin resistant strains are increasingly problematic. Furthermore, drug development for other Gram+ pathogens such as non-tuberculosis mycobacteria, nocardia, corynebacteria, and proprionobacteria is virtually non-existent. New development strategies are needed to treat infections caused by these resistant organisms.

Clinical antibiotics target limited pathways, but none currently target signal transduction. Protein kinases and phosphatases are critical in transducing cellular and environmental signals to trigger growth and division, or to respond to stress and environmental changes. Protein kinases generally have a role in promoting cellular growth, whereas phosphatases generally have an opposing effect on growth. Aberrant regulation of both in human cells is involved in cancer, autoimmune disease, neurodegenerative disorders, and heart disease. Additionally, many protein kinases are critical regulatory molecules in pathogenic bacteria, fungi, viruses, and protozoa. There is an urgent need for more clinically useful drugs targeting specific protein kinases and phosphatases implicated in these diseases.

Human growth signaling cascades regulated by protein kinases are well studied, but bacterial signaling is much less known, especially with respect to drug development. The Actinobacteria and Firmicute families contain conserved eukaryotic-like protein kinases involved in virulence and disease progression. The most well studied of this class are the Penicillin-binding And Serine/Threonine Associated (PASTA) kinases. These kinases consist of an N-terminal cytoplasmic kinase domain which is tethered to a single transmembrane helix to connect to extracellular PASTA domains. The kinase domain has high structural homology to classic "Hanks-like" eukaryotic serine-threonine kinases; however unlike eukaryotic S/T kinases, PASTA kinases can phosphorylate tyrosine and cysteine in addition to serine and threonine. The kinase domain is highly conserved among actinobacteria and firmicutes, but the PASTA domains are more variable. The PASTA domains consist of 1-3 domains with structural homology to penicillin binding proteins and may contain a variable C-terminal domain with an immunoglobulin like fold or PASTA domain. The PASTA domains are known to bind muropeptides and lipid II but are not known to definitively bind β-lactams. PASTA kinases localize to areas of cell wall remodeling and growth, and this localization is thought to increase local concentration of the cytosolic kinase domains and allow them to activate each other by trans-autophosphorylation. Once activated, the kinases phosphorylate several diverse substrates involved in growth, metabolism, stress responses, and virulence. Genetic deletions of PASTA kinases in several species increase β-lactam susceptibility, suggesting a promising target for drug therapy.

The PASTA kinase from *Mycobacteria tuberculosis* (PknB) is the most well studied as it is an essential protein necessary for bacterial survival and growth, making it an attractive drug target. PknB phosphorylates a wide range of critical substrates including the TCA regulator GarA, mycolic acid synthesis protein MabA55, and cell division proteins GlmU56 and Wag31. Pharmacological inhibition of PknB also synergizes with β-lactams to promote mycobacterial cell death by a yet unknown mechanism. This suggests that not only is PknB an attractive stand-alone drug target, but a dual therapy could be employed to lower the dose of each drug needed and reduce the likelihood of resistance development. Accordingly, there is a long felt need in the medical field for more effective therapeutic compounds and more diverse methods of therapy in this area.

SUMMARY OF THE INVENTION

The present invention relates to the inventors' identification of protein kinase inhibitors which exploit subtle structural differences between human kinases and bacterial PASTA kinases to improve specificity and activity. The inventors determined that specificity and activity of respective inhibitors were modulated by, e.g., positioning particular inhibitor moieties in the back pocket of the kinase active site as well as exploiting differences in PASTA kinase ATP binding floors. These compounds offer a new and effective treatment option for several difficult-to-treat human pathogens.

Accordingly, in a first aspect, the invention provides a compound having the chemical structure:

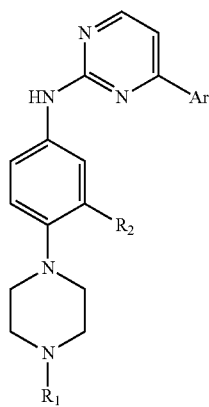

wherein:
$R_1$=Me, Et, n-Pr, —$CH_2CH_2OH$, —$CH_2CH_2OP(O)(OH)_2$, —$CH_2CH_2NMe_2$;
$R_2$=H, Me, Et, o-Pr, i-Pr, $CF_3$, Cl, OMe;
$R_3$=H, Me, NHMe, NHBn, Cl, $NO_2$OMe, F, CN; and
Ar=

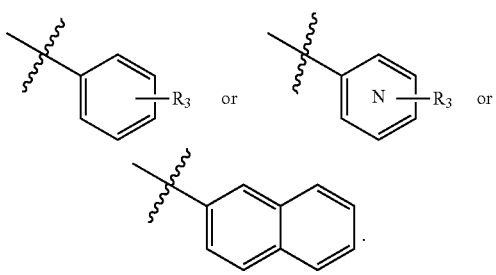

In some embodiments, the compound has any one of the chemical structures shown in FIGS. 5a-5nn.

A compound according to the invention is functionally-characterized by its ability to inhibit a protein kinase, preferably a Penicillin-binding And Serine/Threonine Associated (PASTA) kinase, including, e.g., PknB.

In another aspect, the invention encompasses a method of inhibiting a protein kinase in a subject, comprising administering to the subject an effective amount of a compound having the chemical structure:

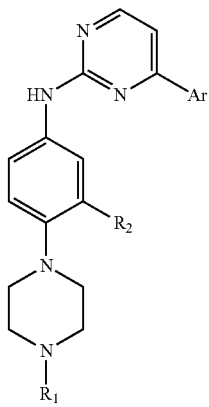

wherein:
$R_1$=Me, Et, n-Pr, —$CH_2CH_2OH$, —$CH_2CH_2OP(O)(OH)_2$, —$CH_2CH_2NMe_2$;
$R_2$=H, Me, Et, o-Pr, i-Pr, $CF_3$, Cl, OMe;
$R_3$=H, Me, NHMe, NHBn, Cl, $NO_2$OMe, F, CN; and
Ar=

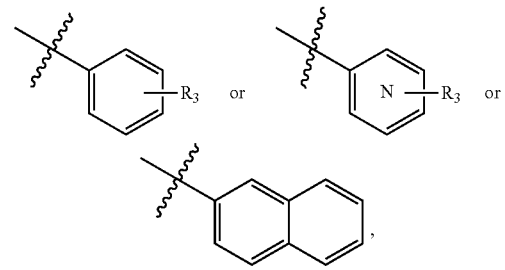

wherein the protein kinase is inhibited in the subject.

Another aspect of the invention provides a method of treating a bacterial infection in a subject, comprising administering an effective amount of compound described and claimed herein to a subject, wherein the bacterial infection is treated in the subject.

In certain embodiments, the bacterial infection comprises a *Mycobacterium tuberculosis* infection.

Methods of treating a bacterial infection according to the invention alternatively include the additional step of administering a β-lactam antibiotic to the subject as a co-therapy in treating the bacterial infection.

As can be appreciated after review of the present disclosure, compounds as described and claimed herein are useful in one more actions including: inhibiting protein kinas activity in a subject; inhibiting a Penicillin-binding And Serine/Threonine Associated (PASTA) kinase in a subject; treating bacterial infection in a subject; and treating a *Mycobacterium tuberculosis* infection in a subject.

Yet another aspect of the invention is directed to a method of treating a bacterial infection in a subject, comprising co-administering an effective amount of a compound as described and claimed herein and an effective amount of an antibiotic (e.g., a beta-lactam antibiotic), wherein the bacterial infection is treated in the subject.

Other objects, features and advantages of the present invention will become apparent after review of the specification, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4a and 4b. Biochemical and microbiologic data for novel aminopyrimidines. This table provides similar data to FIG. 2 with data for additional compounds.

FIG. 6. The utility of FIGS. 5a-5nn is shown in PknB biochemical inhibition by ATP competition (Glo).

FIG. 7. The utility of FIGS. 5a-5nn is shown in PknB physical binding (MST).

FIG. 8. Microbiological Data demonstrating the utility of the present compounds against Mtb auxotroph activity without β-lactams.

FIG. 9. Cdk2 biochemical inhibition by ATP competition (Glo).

FIG. 10. Toxicity Data for the present compounds in zebrafish.

FIG. 11. Toxicity Data for the present compounds in mouse primary macrophage cell toxicity.

DETAILED DESCRIPTION OF THE INVENTION

Figure 1:
FIG. 1. Biochemical and microbiologic data for pyrazolopyridazine aminopyrimidines. The core scaffold is shown with variable R1 and R2 attachments and their corresponding IC50 values against M.tb PknB in an ATP Glo® assay. % inhibition of Stk1 was estimated by 32P autoradiography. As a comparator, % inhibition of PknB was calculated from the experimentally determined IC50 values by normalizing to GW779439X. The MIC of *S. aureus* USA300 was assessed by OD600 for each compound in the presence of sub-lethal (8 µg/mL) oxacillin. Values along with the SEM for each as appropriate are given.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described.

The disclosed compound formulas and structures can in some cases vary between neutral, acid, and/or basic salt forms, depending on the surrounding environment, and such forms may be used interchangeably herein. As a non-limiting example, a primary amine moiety on a compound may be interchangeably designated as —$NH_2$ or as $NH_3^+$. Furthermore, a given compound may have equivalent resonance structures, which may be used interchangeably herein. Finally, a number of the disclosed compounds may exist as multiple enantiomers having different biological/biochemical effects. Herein, all structures that are drawn as a single enantiomer or without a designated stereochemistry encompass all possible enantiomers of the structure.

All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, the term "administering" refers to bringing a subject, tissue, organ or cells in contact with one or more of the kinase inhibitors described in this disclosure. In certain embodiments, the present invention encompasses administering the compounds useful in the present invention to a patient or subject. A "subject," "patient" and "individual," used equivalently herein, refers to a mammal, preferably a human.

As used herein, the terms "effective amount" and "therapeutically effective amount" refer to the quantity of active therapeutic agents sufficient to yield a desired therapeutic response without undue adverse side effects such as toxicity, irritation, or allergic response. The specific "effective amount" will, obviously, vary with such factors as the particular condition being treated, the physical condition of the patient, the duration of the treatment, the nature of concurrent therapy (if any), and the specific formulations employed. In this case, an amount would be deemed therapeutically effective if it results in reduction of a protein kinase activity. The optimum effective amounts can be readily determined by one of ordinary skill in the art using routine experimentation.

There are few antibiotics left to treat drug resistant bacteria, and there is no existing technology to re-sensitize MRSA to β-lactams. In some embodiments, compositions of this invention are used to treat infections by drug-resistant strains of bacteria. By "drug-resistant" it is meant that the bacteria are resistant to treatment with one or more conventional antibiotics. However, the disclosed method may result in improved therapies for treating any Gram-positive bacterial infection that is typically treated with β-lactams, including without limitation infections caused by *Listeria monocytogenes, Staphylococcus aureus* (including MSRA), *Streptococcus pneumoniae, Mycobacterium tuberculosis* and other mycobacteria, *Nocardia*, including the pan resistant *N. farcinia, Clostridium*, and enterococci. The target of the kinase inhibitors (Stk1) is phylogenetically distinct in Gram-negative and Gram-positive bacteria; so the disclosed compounds can selectively inhibit Gram-positive bacteria (and not act against the Gram-negative flora of the human gut), a potentially useful characteristic.

While the present compounds are useful as stand-alone therapeutics, in certain embodiments, the disclosed compounds may be administered prior to, simultaneously with, or subsequent to a β-lactam antibiotic ("co-administration"). The kinase inhibitor and antibiotic may be administered separately by different routes, if desired. As used herein, the term "co-administered" is used to denote simultaneous or sequential administration. Preferably, such co-administration produces a synergistic effect. The terms "synergy" and "synergistic effect" indicate that the effect produced when two or more drugs are co-administered is greater than would be predicted based on the effect produced when the compounds are administered individually. In general, a synergistic effect is most clearly demonstrated at sub-optimal concentrations of the compounds (i.e., sub-therapeutic dosages). A lower dosage minimizes the potential of side effects, thereby providing an increased margin of safety. Synergy can result in lower cytotoxicity, increased antimicrobial effect, or some other beneficial effect of the combination compared with the individual components.

In one embodiment, the disclosed compounds are co-administered with a β-lactam antibiotic. In some embodiments, one or more of the disclosed compounds are co-administered with an antibiotic selected from the group consisting of benzathine penicillin, benzylpenicillin (penicillin G), phenoxymethylpenicillin (penicillin V), procaine penicillin, methicillin, oxacillin, nafcillin, cloxacillin, dicloxacillin, flucloxacillin, temocillin, amoxicillin, ampicillin, co-amoxiclav, azlocillin, carbenicillin, ticarcillin, mezlocillin, piperacillin, cephalosporins, cephalexin, cephalothin, cefazolin, cefaclor, cefuroxime, cefamandole, cephamycins, cefotetan, cefoxitin, ceftriaxone, cefotaxime, cefpodoxime, cefixime, ceftazidime, cefepime, cefpirome, imipenem, meropenem, ertapenem, faropenem, doripenem, monobactams, aztreonam, tigemonam, nocardicin A, and tabtoxinine-P-lactam.

In some embodiments, the disclosed compounds and the antibiotic will be administered by the same route and in a single composition, so as to ensure that they are given simultaneously to the subject. In some embodiments, the disclosed compounds and the antibiotic will be administered by different routes and in separate compositions, for example to improve stability and/or efficacy.

The disclosure also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Figure 3:
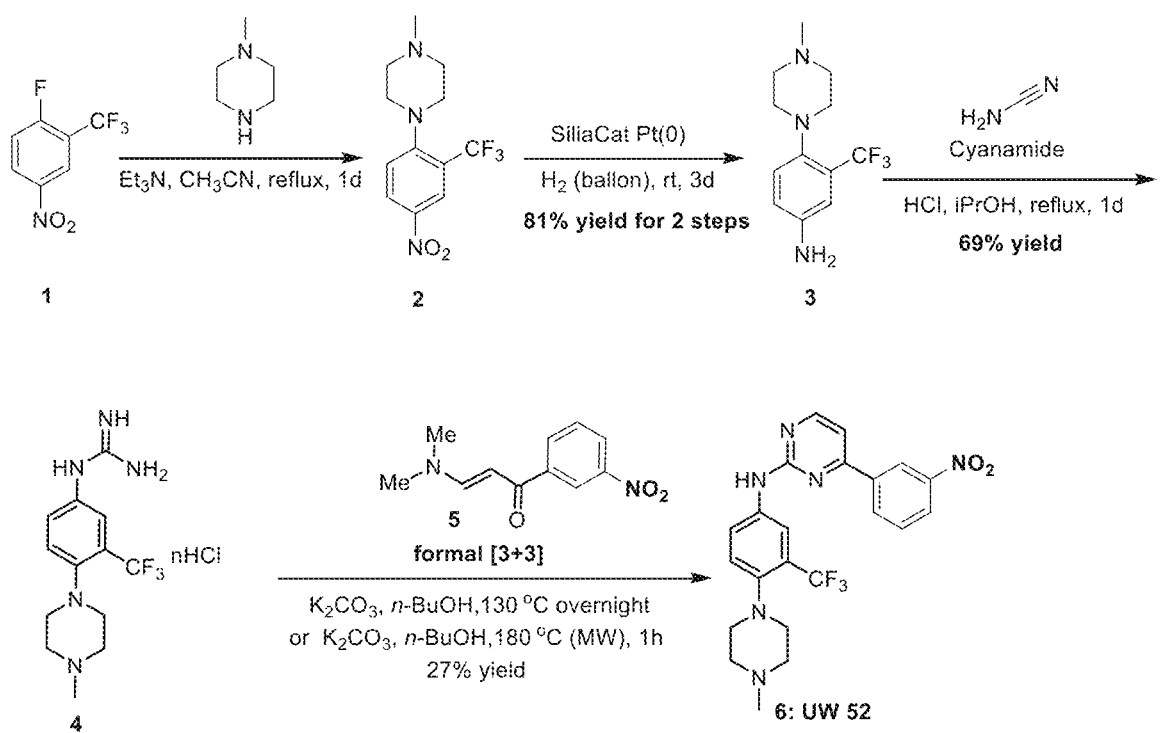
FIG. 3. Synthesis of UW 52 from vinylogous amide [3+3] cycloaddition.
Figure 5A:
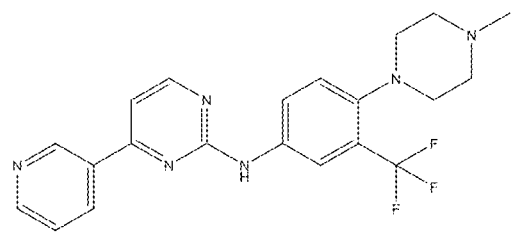
FIGS. 5a-5nn. Provides the chemical structure for the additional compounds of FIGS. 4a and 4b.
Figure 5B:
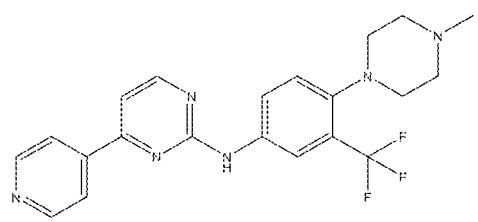
Figure 5C:
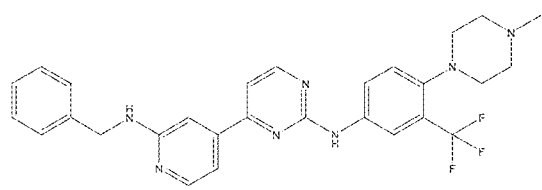
Figure 5D:
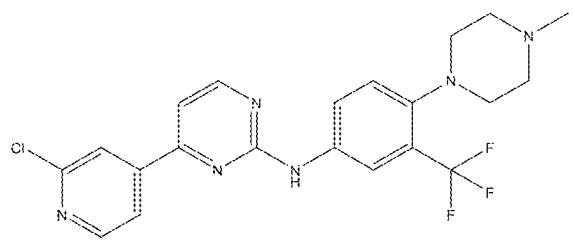
Figure 5E:
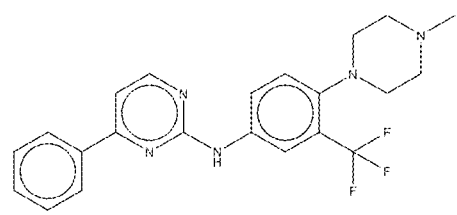
Figure 5F:
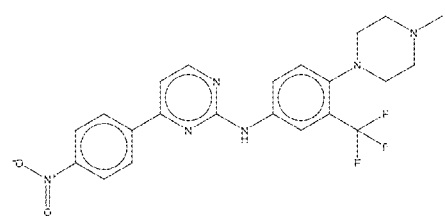
Figure 5G:
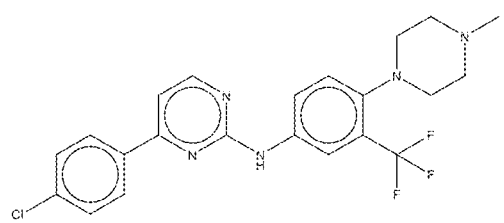
Figure 5H:
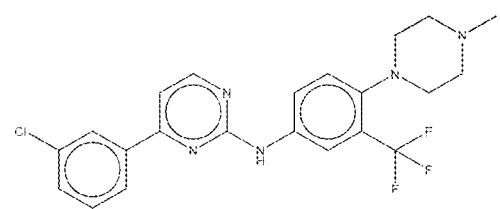
Figure 5I:
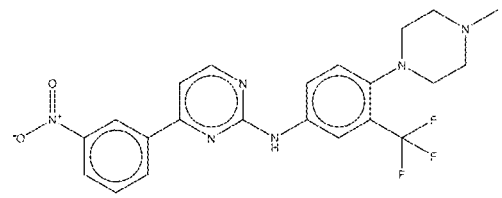
Figure 5J:
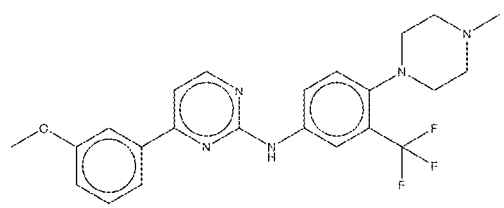
Figure 5K:
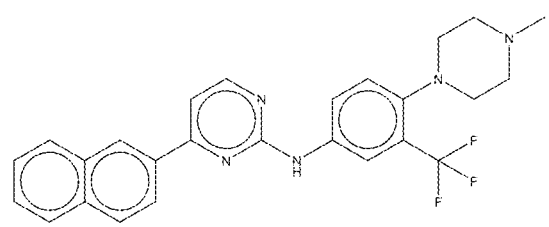
Figure 5L:
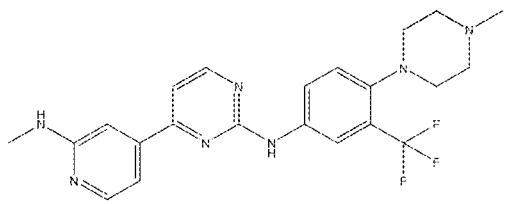
Figure 5M:
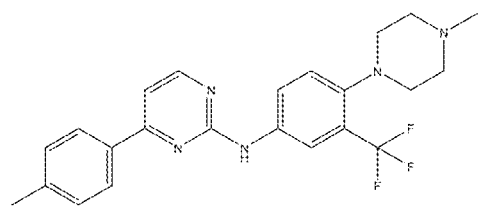
Figure 5N:
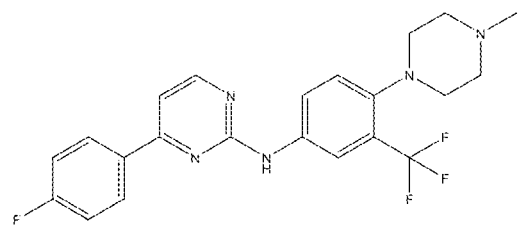
Figure 5O:
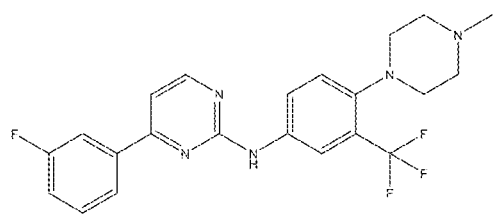
Figure 5P:
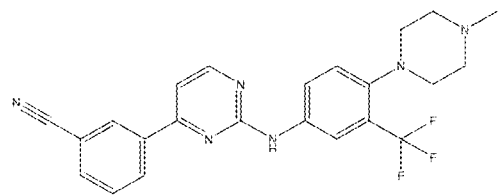
Figure 5Q:
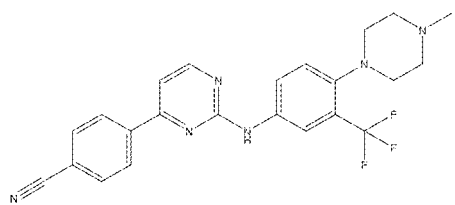
Figure 5R:
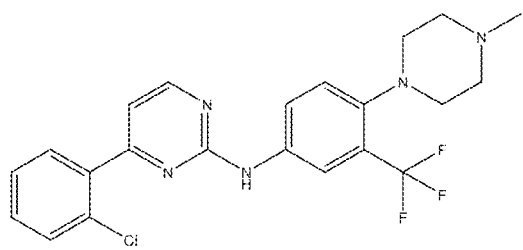
Figure 5S:
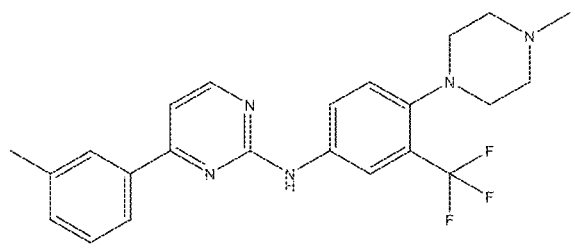
Figure 5T:
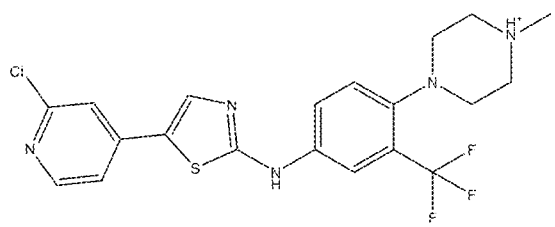
Figure 5U:
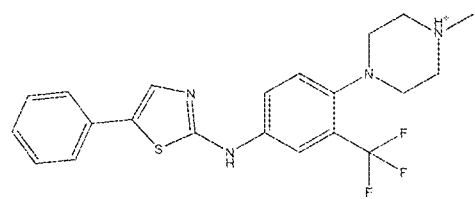
Figure 5V:
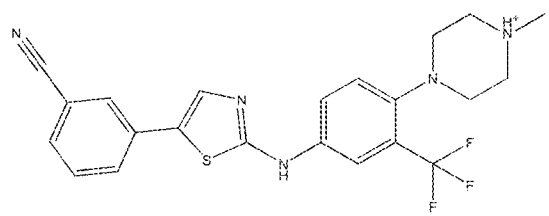
Figure 5W:
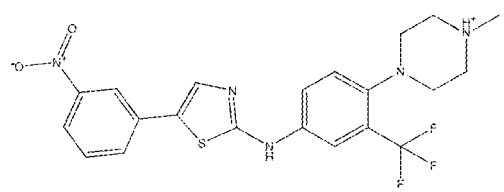
Figure 5X:
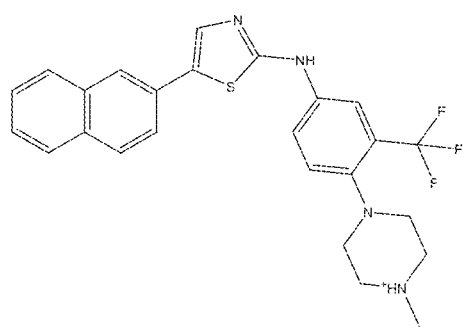
Figure 5Y:
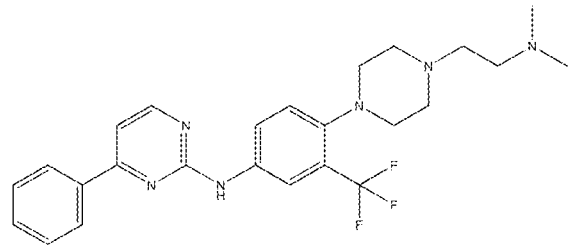
Figure 5Z:
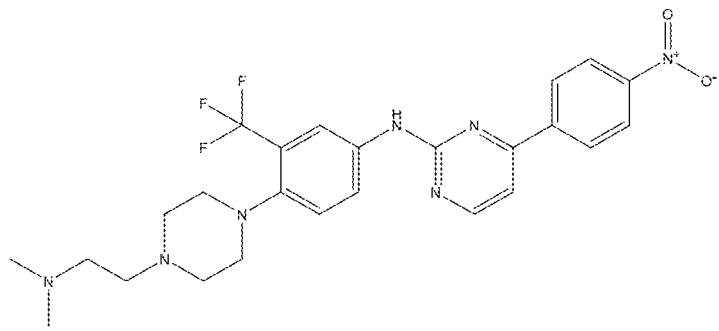
Figure 5A:
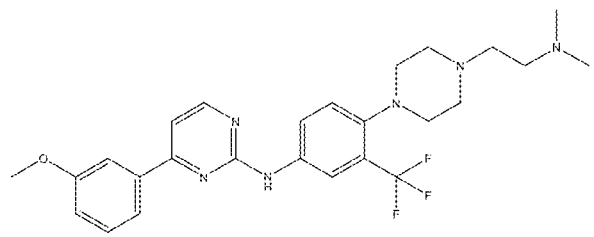
Figure 5B:
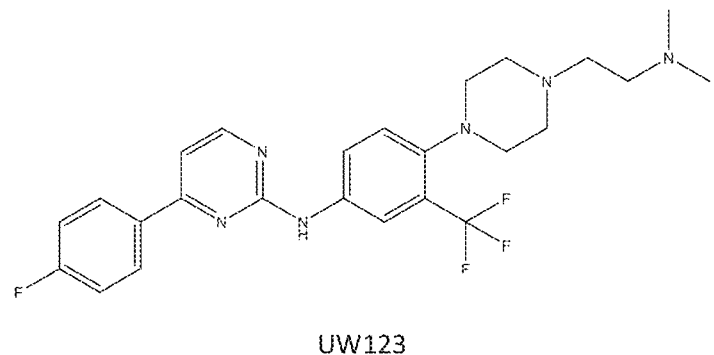
Figure 5C:
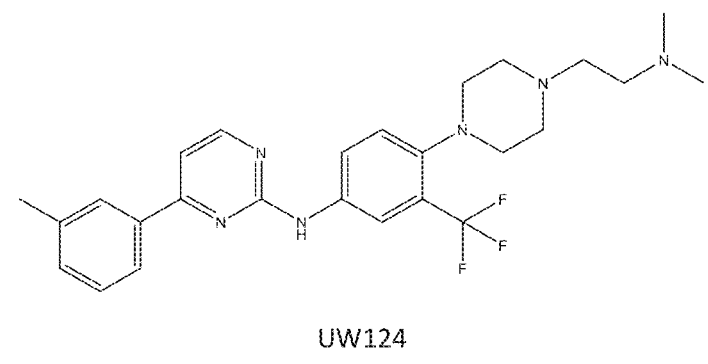
Figure 5D:
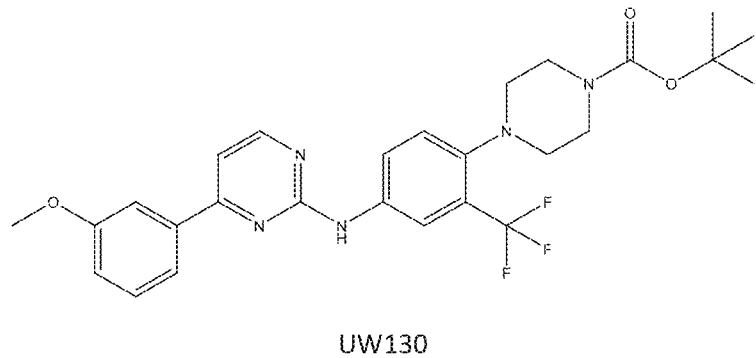
Figure 5E:
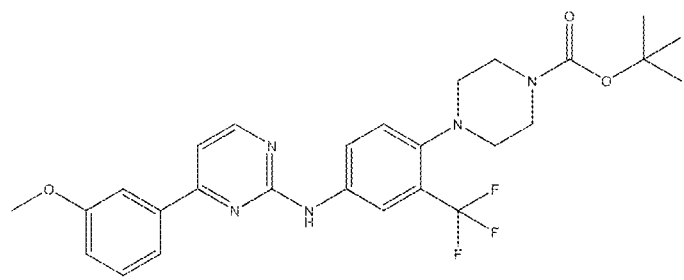
Figure 5F:
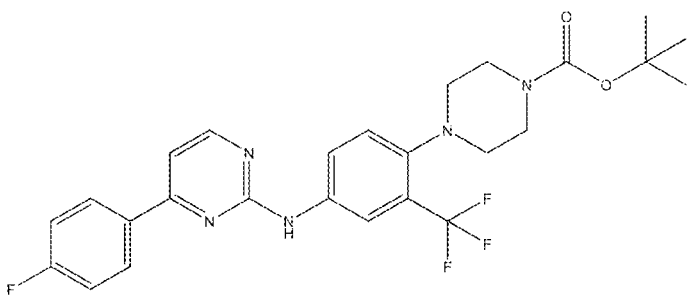
Figure 5G:
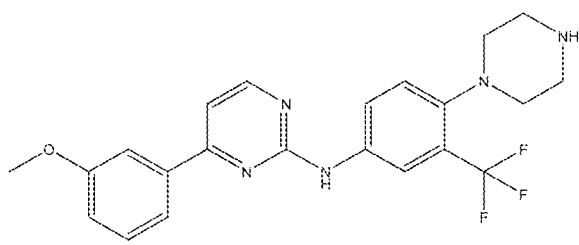
Figure 5H:
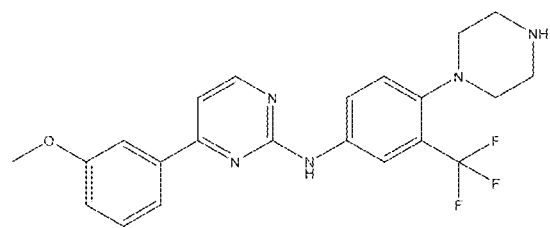
Figure 5I:
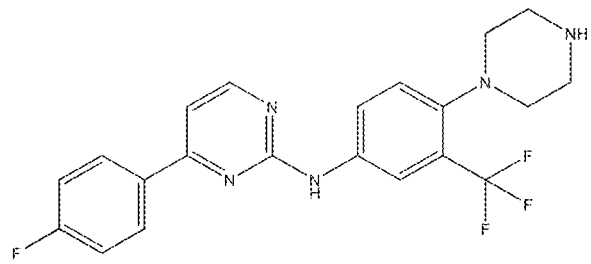
Figure 5J:
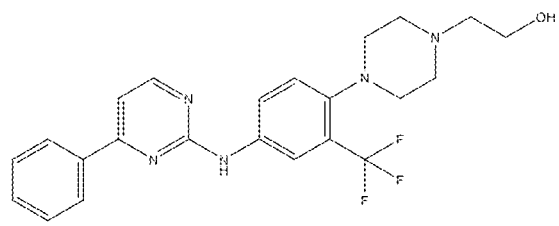
Figure 5K:
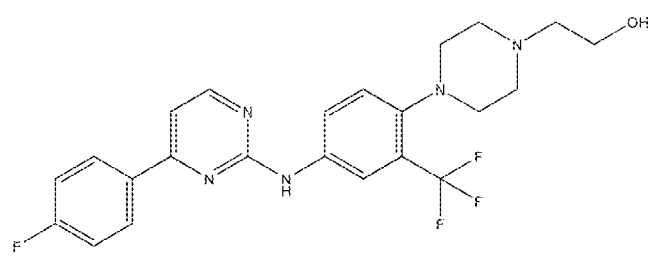
Figure 5L:
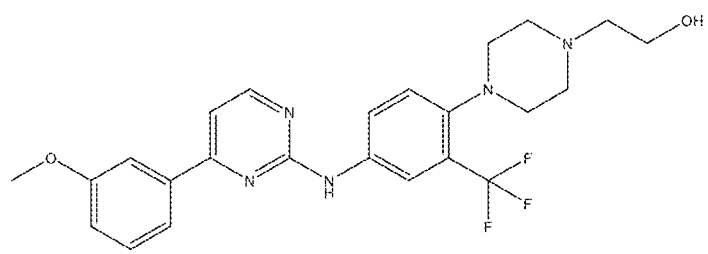
Figure 5M:
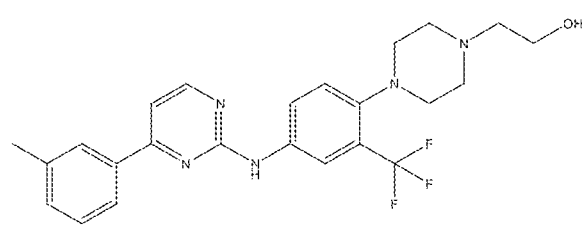
Figure 5N:
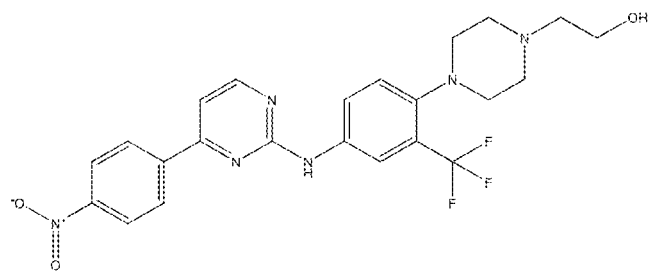

As described below, the strategy for improving on-target PknB activity as well as MIC of GW779439X derivatives was to exchange the pyridazine head group for a variety of arenes, probing the impact of both the steric and electronic effects of aryl substituents. The synthesis of UW 52 is shown (FIG. 3), with key formal [3+3] cycloaddition between aryl guanidine 4 and vinylogous amide 5, affording the desired aminopyrimidine 6. Notably, this late-stage functionalization approach can be utilized to explore the structure-activity relationships of new AP compounds on Stk1 and MRSA activity. Vinylogous amides related to 5 can be readily sourced direct from commercial sources, or a via simple 1-step preparation from the aryl methyl ketones.

Example 1: Optimization of Stk1 Inhibitors

GW779439X has potent PknB and Stk1 activity and is microbiologically active. MRSA was screened against a small library of kinase inhibitors, and an aminopyrimidine, GW779439X, was discovered which microbiologically inhibited MRSA when combined with a β-lactam. Subsequent analysis revealed that it and five other related compounds had appreciable biochemical and microbiological activity (FIG. 1).

GW779439X was docked in PknB and Stk1 following published procedures, and they were predicted to bind similarly and with favorable contacts. Subsequent testing revealed GW779439X and related compounds had potent PknB activity (FIG. 1), and this suggested some similar structure activity relationships (SAR) between the kinases exist. Collectively, these data show this family of compounds can enter different bacterial cells and bind to areas conserved in both kinases.

Figure 2:
FIG. 2. Biochemical and microbiologic data for novel aminopyrimidines. The core scaffold is shown with variable R1 attachments and their corresponding IC50 values against M.tb PknB in an ATP Glo® assay as well as binding affinity from microscale thermophoresis and MIC of an M.tb auxotroph assessed by resazurin reduction. Values along with the SEM for each as appropriate are given. Eight-point curves were done for each assay. IP=in progress; ND=not determined.

Example 2: Novel Aminopyrimidines have Variable PknB Activity but Improved Microbiological Activity Compounds were tested for PknB activity either using the ATP Glo® assay as described or by direct binding using microscale thermophoresis (NanoTemper Technologies) (FIG. 2). Compounds were also tested microbiologically against an auxotrophic *M. tuberculosis* following published procedures. The compounds displayed a surprising range of biochemical and microbiological activity, though 14 out of 20 were microbiologically better than GW779439X (FIG. 2, FIGS. 4a and 4b, FIG. 6 (PknB inhibition by ATP competition assay), FIG. 7 (PknB physical binding), FIG. 8 (*M. tuberculosis* auxotroph activity without beta-lactam antibiotic), FIG. 9 (Cdk2 inhibition by ATP competition assay), FIG. 10 (Toxicity in zebra fish), and FIG. 11 (Toxicity in mouse primary macrophage cells)). It is unclear whether this is due to off target effects on one of the other 10 serine threonine kinases in *M. tuberculosis* or improved cellular accumulation, but this is difficult to test since PknB is essential and a genetic knockout is not viable. Three Boc-protected intermediates were tested (UW130 shown) and all showed no appreciable activity toward the kinase or bacteria, suggesting a functional role for the protonated methylpiperidine. These data show the ability to create novel compounds in this class with potential for improved microbiological activity and possible activity against other kinases.

Example 3: Novel Aminopyrimidines Dock Favorable to Stk1

Proposed and synthesized inhibitors were docked to PknB and Stk1 as described above. The inhibitors were predicted to bind in the same alignment as the GW779439X core. Furthermore, several of the synthesized inhibitors scores were higher than or near GW779439X suggesting potential for similar activity. The alignment suggests a conserved binding mode, but crystal structures are needed to confirm.

Example 4

Compound Synthesis and Identification

All reactants and reagents were ACS reagent grade or better, and were purchased from Sigma-Aldrich, Combi-Blocks, Ark Pharm, Matrix Scientific, Alfa Aesar, Enamine, Astatech, or Oakwood Chemical, and used without further purification. All reactions in non-aqueous media were conducted under a positive pressure of dry argon in glassware that had been dried in oven prior to use unless noted otherwise. Anhydrous solutions of reaction mixtures were transferred via an oven dried syringe or cannula. All solvents were dried prior to use unless noted otherwise. Thin layer chromatography was performed using precoated silica gel plates (EMD Chemical Inc. 60, F254). Microwave reactions were performed on an Anton Paar Monowave 300 system in G10 vials. Flash column chromatography was performed with silica gel (RediSep Rf Gold, 20-40 μm) on a Teledyne Isco CombiFlash system. Prep-HPLC chromatography was performed on a Teledyne Isco RediSep Prep C18 column (5 μm, 100 Å, 20×150 mm) on a Teledyne Isco EZ-Prep system. 1H nuclear magnetic resonance spectra (NMR) were obtained on a Bruker 400 MHz or Varian Unity-Inova 500 MHz recorded in ppm (δ) downfield of TMS (δ=0) in CDCl3, Methanol-d4, unless noted otherwise. Signal splitting patterns were described as singlet (s), doublet (d), triplet (t), quartet (q), quintet (quint), or multiplet (m), with coupling constants (J) in hertz. The liquid chromatography mass spectrometry LC-MS analysis of final products was processed on Agilent 1290 Infinity II LC system using Poroshell 120 EC-C18 column (5 cm×2.1 mm, 1.9 μm) for chromatographic separation. Agilent 6120 Quadrupole LC/MS with multimode Electrospray Ionization plus atmospheric pressure chemical ionization (MM-ES+APCI) was used for detection. The mobile phases were 5.0% methanol and 0.1% formic acid in purified water (A) and 0.1% formic acid in methanol (B). The gradient was held at 5% (0-0.2 min), increased to 100% at 2.5 min, then held at isocratic 100% B for 0.4 min and then immediately stepped back down to 5% for 0.1 min re-equilibration. The flow rate was set at 0.8 mL/min. Column temperature was set at 40° C. The purities of all the final compounds were determined to be over 95% by LCMS.

General Method A

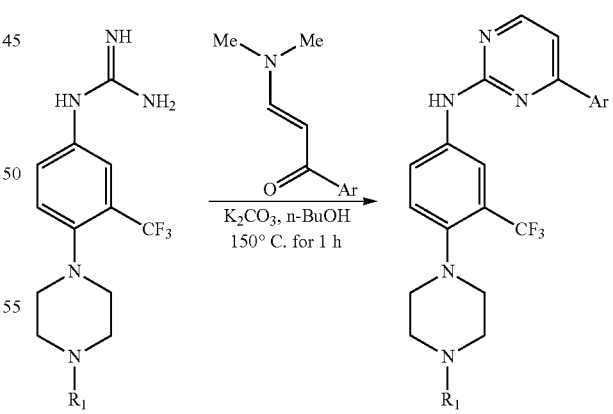

General method A: To a solution of (2E)-3-(dimethylamino)-1-(aryl-3-yl)prop-2-en-1-one (0.2 mmol) and N-[4-(4-alkylpiperazin-1-yl)-3-(trifluoromethyl)phenyl]guanidine (0.24 mmol, 1.2 equiv) in n-butanol (2 mL) was added K₂CO₃ (0.6 mmol, 3 equiv.) and stirred at 150° C. (MW) for 1 h. The mixture was purified by reverse phase Prep-HPLC column with water/acetonitrile gradient.

General Method B

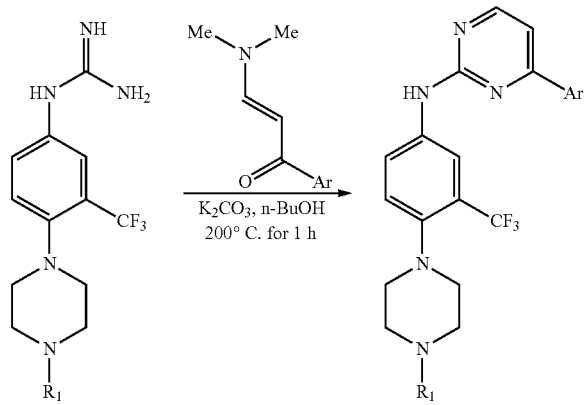

General method B: To a solution of (2E)-3-(dimethyl-amino)-1-(aryl-3-yl)prop-2-en-1-one (0.4 mmol) and N-[4-(4-alkylpiperazin-1-yl)-3-(trifluoromethyl)phenyl]guanidine (0.48 mmol, 1.2 equiv) in n-butanol (5 mL) was added K$_2$CO$_3$ (2 mmol, 5 equiv.) and stirred at 200° C. (MW) for 1 h. The mixture was purified by reverse phase Prep-HPLC column or flash column.

General Method C

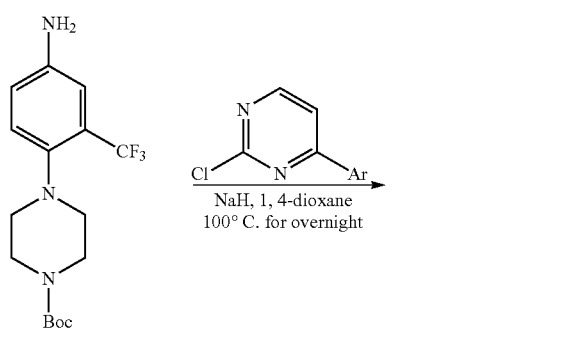

General method C: To a solution of tert-butyl 4-[4-amino-2-(trifluoromethyl)phenyl]piperazine-1-carboxylate (0.2 mmol) in 1,4-dioxane (2 mL) was added NaH (0.4 mmol, 2 equiv.) and stirred at 0° C. for 30 min. Then 2-chloro-4-arylpyrimidine was added to the mixture and then heated to 100° C. overnight. The mixture was purified by reverse phase Prep-HPLC column with water/acetonitrile gradient.

General Method D

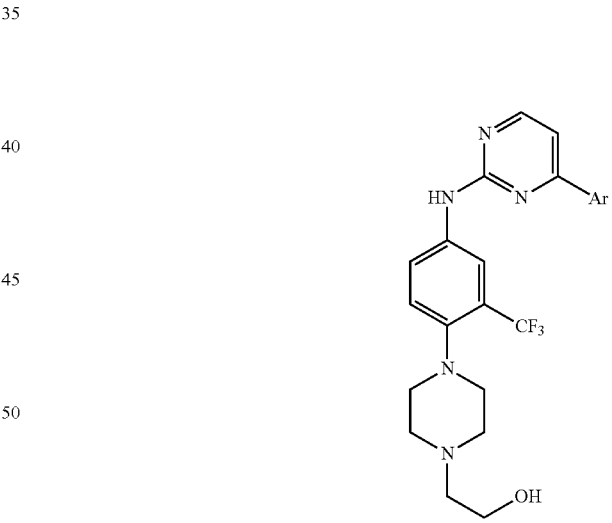

General method D: To a solution of 2-{4-[4-amino-2-(trifluoromethyl)phenyl]piperazin-1-yl}ethan-1-ol (0.2 mmol) and 2-chloro-4-arylpyrimidine (0.2 mmol) in n-butanol (2 mL) was added TsOH (0.4 mmol, 2 equiv.) and stirred at 150° C. (MW) for 1 h. The mobile phases were 0.1% formic acid in purified water (A) and 0.1% formic acid in acetonitrile (B). The gradient was held at 10% B (0-2 min), increased to 50% B at 25 min and held at isocratic 50% B for 10 min, then increased to 100% at 35 min and held at isocratic 100% B for 10 min, then immediately stepped back down to 80% for 2 min re-equilibration.

Synthetic Schemes

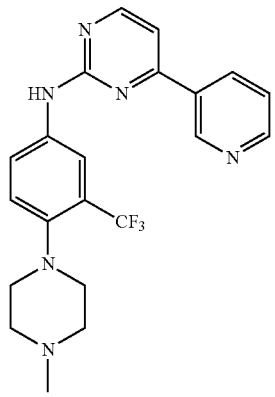

N-(4-(4-methylpiperazin-1-yl)-3-(trifluoromethyl)phenyl)-4-(pyridin-3-yl)pyrimidin-2-amine (UW011) General method A. 54% yield. $^1$H NMR (500 MHz, Chloroform-d) δ 9.25 (d, J=2.3 Hz, 1H), 8.72 (dd, J=4.8, 1.7 Hz, 1H), 8.49 (d, J=5.1 Hz, 1H), 8.40-8.37 (m, 1H), 8.33 (s, 1H), 8.22 (d, J=2.7 Hz, 1H), 7.78 (dd, J=8.6, 2.6 Hz, 1H), 7.47 (dd, J=8.0, 4.8 Hz, 1H), 7.41 (d, J=8.6 Hz, 1H), 7.23 (d, J=5.2 Hz, 1H), 3.17 (s, 8H), 2.75 (s, 3H). LRMS (ESI): m/z 415.2 [M+H]$^+$.

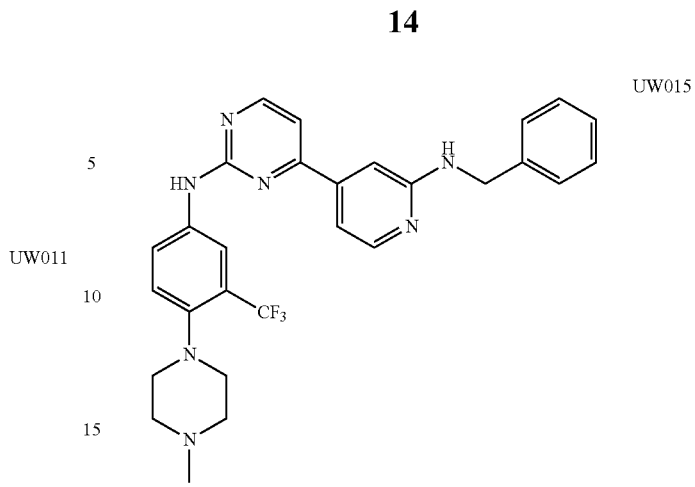

4-(2-(benzylamino)pyridin-4-yl)-N-(4-(4-methylpiperazin-1-yl)-3-(trifluoromethyl)phenyl)pyrimidin-2-amine (UW015) To a solution of 4-(2-chloropyridin-4-yl)-N-[4-(4-methylpiperazin-1-yl)-3-(trifluoromethyl)phenyl]pyrimidin-2-amine (50 mg, 0.111 mmol) in EtOH was added 1-phenylmethanamine (0.556 mmol, 5 equiv.) and stirred at 180° C. (MW) for 3 h. $^1$H NMR (500 MHz, Chloroform-d) δ 8.49 (d, J=5.2 Hz, 1H), 8.22 (d, J=2.6 Hz, 1H), 8.15 (d, J=5.5 Hz, 1H), 7.98 (s, 1H), 7.73 (dd, J=8.6, 2.6 Hz, 1H), 7.42-7.33 (m, 5H), 7.31-7.28 (m, 1H), 7.16 (dd, J=5.6, 1.5 Hz, 1H), 7.13-7.10 (m, 2H), 4.59 (s, 2H), 3.23 (s, 8H), 2.73 (s, 3H). LRMS (ESI): m/z 520.3 [M+H]$^+$.

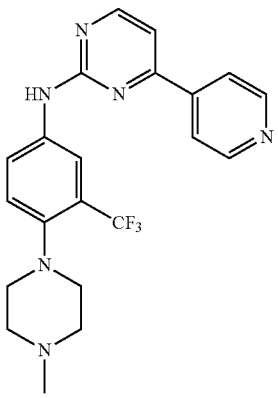

N-(4-(4-methylpiperazin-1-yl)-3-(trifluoromethyl)phenyl)-4-(pyridin-4-yl)pyrimidin-2-amine (UW012) General method A. 51% yield. $^1$H NMR (500 MHz, Chloroform-d) δ 8.82-8.75 (m, 2H), 8.54 (d, J=5.1 Hz, 1H), 8.38 (s, 1H), 8.27 (d, J=2.6 Hz, 1H), 7.96-7.91 (m, 2H), 7.76 (dd, J=8.7, 2.6 Hz, 1H), 7.42 (d, J=8.6 Hz, 1H), 7.28-7.24 (m, 1H), 3.19 (s, 8H), 2.77 (s, 3H). LRMS (ESI): m/z 415.2 [M+H]$^+$.

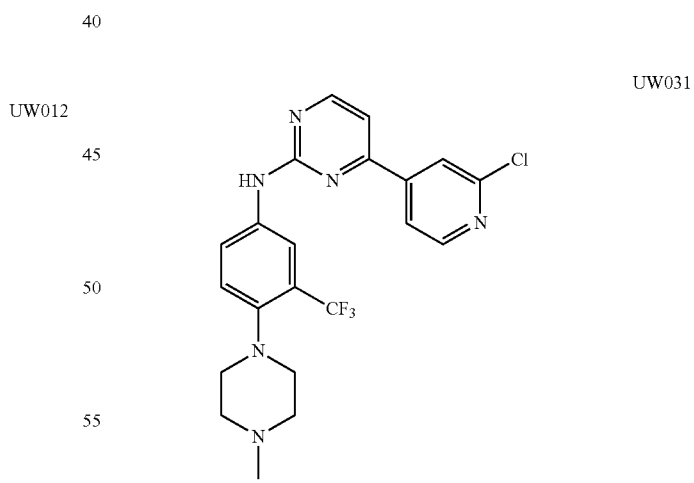

4-(2-chloropyridin-4-yl)-N-(4-(4-methylpiperazin-1-yl)-3-(trifluoromethyl)phenyl)pyrimidin-2-amine (UW031) General method A. 34% yield. $^1$H NMR (500 MHz, Chloroform-d) δ 8.58 (t, J=5.7 Hz, 2H), 8.30 (s, 1H), 8.03 (s, 1H), 7.98 (s, 1H), 7.84 (dd, J=5.2, 1.7 Hz, 1H), 7.72 (dd, J=8.7, 2.6 Hz, 1H), 7.46 (d, J=8.7 Hz, 1H), 7.25 (dd, J=5.1, 1.5 Hz, 1H), 3.23 (s, 8H), 2.81 (s, 3H). LRMS (ESI): m/z 449.1 [M+H]$^+$.

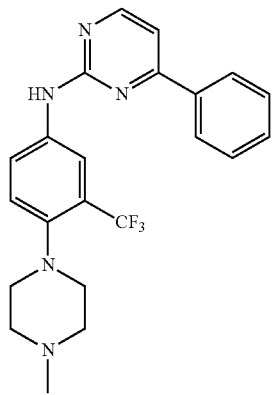

UW042

N-(4-(4-methylpiperazin-1-yl)-3-(trifluoromethyl)phenyl)-4-phenylpyrimidin-2-amine (UW042) General method A. 85% yield. $^1$H NMR (500 MHz, Chloroform-d) δ 8.63 (s, 1H), 8.39 (d, J=5.3 Hz, 1H), 8.25 (d, J=2.6 Hz, 1H), 8.05-8.00 (m, 2H), 7.76 (dd, J=8.7, 2.6 Hz, 1H), 7.49-7.45 (m, 3H), 7.36 (d, J=8.7 Hz, 1H), 7.17 (d, J=5.2 Hz, 1H), 3.15 (s, 8H), 2.75 (s, 3H). LRMS (ESI): m/z 414.0 [M+H]$^+$.

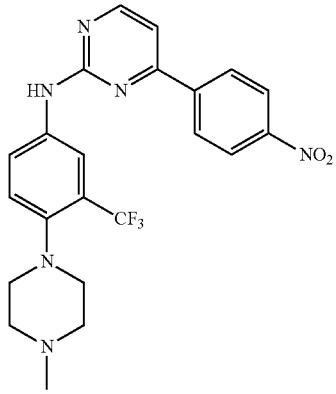

UW048

N-(4-(4-methylpiperazin-1-yl)-3-(trifluoromethyl)phenyl)-4-(4-nitrophenyl)pyrimidin-2-amine (UW048) General method A. 43% yield. $^1$H NMR (500 MHz, Methylene Chloride-d$_2$) δ 8.56 (d, J=5.1 Hz, 1H), 8.38-8.31 (m, 3H), 8.28-8.24 (m, 3H), 7.75 (d, J=7.6 Hz, 1H), 7.59 (s, 1H), 7.45 (d, J=8.3 Hz, 1H), 7.29 (d, J=5.1 Hz, 1H), 3.45 (s, 8H), 2.57 (s, 3H). LRMS (ESI): m/z 459.2 [M+H]$^+$.

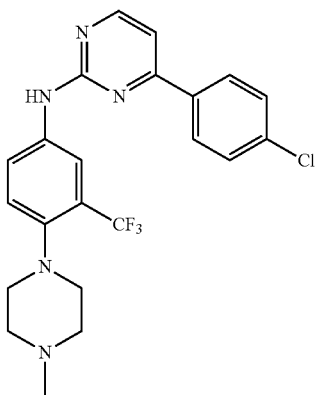

UW049

4-(4-chlorophenyl)-N-(4-(4-methylpiperazin-1-yl)-3-(trifluoromethyl)phenyl)pyrimidin-2-amine (UW049) General method A. 57% yield. $^1$H NMR (500 MHz, Chloroform-d) δ 8.47 (d, J=5.2 Hz, 1H), 8.27 (d, J=2.6 Hz, 1H), 8.04-8.01 (m, 2H), 7.74 (dd, J=8.6, 2.6 Hz, 1H), 7.69 (s, 1H), 7.51-7.48 (m, 2H), 7.44 (d, J=8.7 Hz, 1H), 7.19 (d, J=5.3 Hz, 1H), 3.17 (s, 8H), 2.70 (s, 3H). LRMS (ESI): m/z 448.0 [M+H]$^+$.

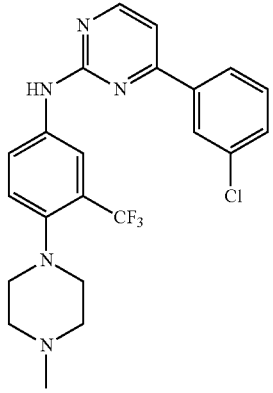

UW051

4-(3-chlorophenyl)-N-(4-(4-methylpiperazin-1-yl)-3-(trifluoromethyl)phenyl)pyrimidin-2-amine (UW051) General method A. 78% yield. $^1$H NMR (500 MHz, Chloroform-d) δ 8.45 (s, 1H), 8.26 (d, J=2.7 Hz, 2H), 8.03 (s, 1H), 7.90 (d, J=7.5 Hz, 1H), 7.70 (dd, J=8.7, 2.6 Hz, 1H), 7.48-7.35 (m, 3H), 7.15 (d, J=5.2 Hz, 1H), 3.16 (s, 8H), 2.73 (s, 3H). LRMS (ESI): m/z 448.0 [M+H]$^+$.

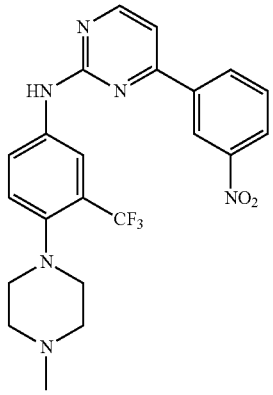

UW052

N-(4-(4-methylpiperazin-1-yl)-3-(trifluoromethyl)phenyl)-4-(3-nitrophenyl)pyrimidin-2-amine (UW052) General method A. 27% yield. $^1$H NMR (500 MHz, Chloroform-d) δ 8.88 (s, 1H), 8.55 (d, J=5.2 Hz, 1H), 8.42 (d, J=7.8 Hz, 1H), 8.36-8.33 (m, 2H), 8.22-8.21 (m, 1H), 8.03 (s, 1H), 7.76 (dd, J=8.6, 2.1 Hz, 1H), 7.70 (t, J=8.0 Hz, 1H), 7.43 (d, J=8.6 Hz, 1H), 7.28 (d, J=5.2 Hz, 1H), 3.18 (s, 8H), 2.73 (s, 2H). LRMS (ESI): m/z 459.1 [M+H]$^+$.

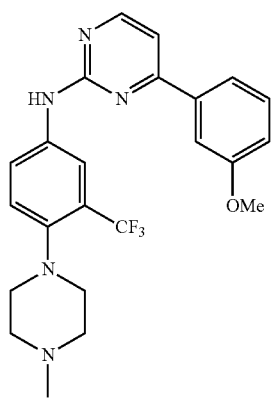

UW055

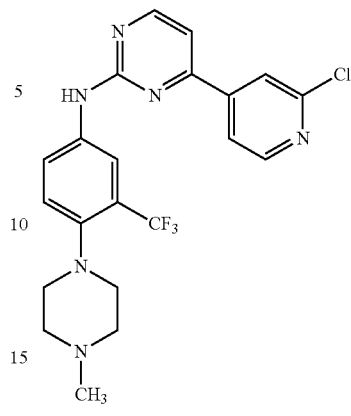

UW031

4-(3-methoxyphenyl)-N-(4-(4-methylpiperazin-1-yl)-3-(trifluoromethyl)phenyl)pyrimidin-2-amine (UW055) General method A. 48% yield. $^1$H NMR (500 MHz, Chloroform-d) δ 8.37 (d, J=5.3 Hz, 1H), 8.31 (s, 1H), 8.25-8.22 (m, 1H), 8.03 (d, J=8.7 Hz, 2H), 7.80-7.75 (m, 2H), 7.38 (d, J=8.6 Hz, 1H), 7.13 (d, J=5.3 Hz, 1H), 6.99 (d, J=8.7 Hz, 2H), 3.86 (s, 3H), 3.14 (s, 8H), 2.69 (s, 3H). LRMS (ESI): m/z 444.0 [M+H]$^+$.

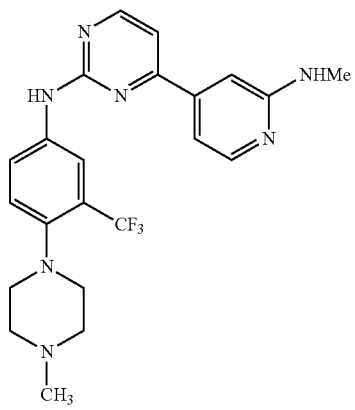

UW107

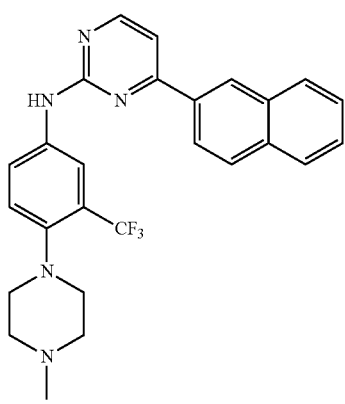

UW059

N-(4-(4-methylpiperazin-1-yl)-3-(trifluoromethyl)phenyl)-4-(naphthalen-2-yl)pyrimidin-2-amine (UW059) General method A. 57% yield. $^1$H NMR (500 MHz, Chloroform-d) δ 8.59 (s, 1H), 8.48-8.44 (m, 3H), 8.10 (d, J=8.4 Hz, 1H), 7.94 (t, J=8.8 Hz, 2H), 7.85 (d, J=5.0 Hz, 1H), 7.70 (d, J=7.8 Hz, 1H), 7.56-7.51 (m, 2H), 7.38 (d, J=8.5 Hz, 1H), 7.32 (d, J=5.1 Hz, 1H), 3.16 (s, 8H), 2.73 (s, 3H). LRMS (ESI): m/z 464.1 [M+H]$^+$.

4-(2-(methylamino)pyridin-4-yl)-N-(4-(4-methylpiperazin-1-yl)-3-(trifluoromethyl)phenyl)pyrimidin-2-amine (UW107) To a sealed tube was added 4-(2-chloropyridin-4-yl)-N-(4-(4-methylpiperazin-1-yl)-3-(trifluoromethyl) phenyl)pyrimidin-2-amine (30 mg, 0.067 mmol) and 30% MeNH$_2$ in EtOH (10 mL). The mixture was stirred at 140° C. for 5 days. After the completion of the reaction, the mixture was concentrated under reduced pressure and purified by EZ-prep (10%-25% MeCN/water+0.1% HCOOH), the product was basified with TEA and flushed with 10% MeOH/DCM. Yield: 15 mg, 51%; yellowish solid. $^1$H NMR (500 MHz, Chloroform-d) δ 8.53 (d, J=5.1 Hz, 1H), 8.23 (d, J=5.3 Hz, 1H), 8.21 (d, J=2.7 Hz, 1H), 7.69 (dd, J=8.7, 2.6 Hz, 1H), 7.62 (s, 1H), 7.39 (d, J=8.6 Hz, 1H), 7.19 (d, J=5.1 Hz, 1H), 7.10 (d, J=4.7 Hz, 2H), 4.89 (s, 1H), 3.01 (s, 3H), 2.97 (t, J=4.8 Hz, 4H), 2.63 (s, 4H), 2.40 (s, 3H). $^{13}$C NMR (126 MHz, Chloroform-d) δ 163.6, 160.5, 160.1, 159.3, 149.1, 146.9, 145.7, 136.7, 128.1 (q, J=29.0 Hz), 125.0, 124.1 (q, J=273.6 Hz), 123.3, 118.1 (q, J=5.5 Hz), 110.3, 109.4, 103.9, 55.6, 53.4, 46.1, 29.3. $^{19}$F NMR (470 MHz, Chloroform-d) δ −60.5. MS (ESI) m/z for $C_{22}H_{25}F_3N_7^+$ (M+H)$^+$, 444.2 (Calc.), found 444.7; LC-MS purity: 97.64%.

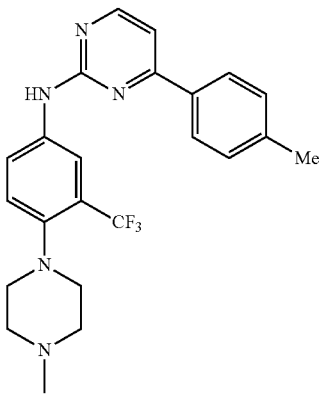

UW108

N-(4-(4-methylpiperazin-1-yl)-3-(trifluoromethyl)phenyl)-4-(p-tolyl)pyrimidin-2-amine (UW108) Method B. The reaction was performed with (E)-3-(dimethylamino)-1-(p-tolyl)prop-2-en-1-one (38 mg, 0.2 mmol), 1-(4-(4-methylpiperazin-1-yl)-3-(trifluoromethyl)phenyl)guanidine (73 mg, 0.24 mmol), K$_2$CO$_3$ (276 mg, 2 mmol) and nBuOH (5 mL). Eluent: EZ-prep (10%-60% MeCN/water+0.1% HCOOH); yield: 16 mg, 19%; white/brownish solid. 1H NMR (400 MHz, Chloroform-d) δ 8.45 (d, J=5.3 Hz, 1H), 8.23 (d, J=2.6 Hz, 1H), 7.98 (d, J=7.9 Hz, 2H), 7.74 (dd, J=8.6, 2.6 Hz, 1H), 7.69 (s, 1H), 7.39 (d, J=8.7 Hz, 1H), 7.31 (d, J=7.9 Hz, 2H), 7.19 (d, J=5.2 Hz, 1H), 3.27-3.00 (m, 4H), 2.82 (s, 4H), 2.51 (s, 3H), 2.43 (s, 3H). 13C NMR (101 MHz, Chloroform-d) δ 165.2, 160.0, 158.5, 145.7, 141.6, 137.5, 134.1, 129.8, 128.1 (q, J=28.5 Hz), 127.2, 125.1, 124.0 (q, J=273.5 Hz), 123.0, 117.7 (q, J=5.8 Hz), 108.7, 54.9, 52.4, 45.1, 21.6. 19F NMR (376 MHz, Chloroform-d) δ −60.7. MS (ESI) m/z for C23H25F3N5+ (M+H)+, 428.2 (Calc.), found 428.1; LC-MS purity: >99%.

4-(4-fluorophenyl)-N-(4-(4-methylpiperazin-1-yl)-3-(trifluoromethyl)phenyl)pyrimidin-2-amine (UW109) Method B. The reaction was performed with (E)-3-(dimethylamino)-1-(4-fluorophenyl)prop-2-en-1-one (77 mg, 0.4 mmol), 1-(4-(4-methylpiperazin-1-yl)-3-(trifluoromethyl)phenyl)guanidine (146 mg, 0.48 mmol), K$_2$CO$_3$ (276 mg, 2 mmol) and nBuOH (5 mL). Eluent: EZ-prep (10%-60% MeCN/water+0.1% HCOOH) followed by normal phase flash column 5% MeOH/DCM; yield: 35 mg, 20%; white solid. $^1$H NMR (400 MHz, Chloroform-d) δ 8.47 (d, J=5.2 Hz, 1H), 8.18 (d, J=2.6 Hz, 1H), 8.11-8.02 (m, 2H), 7.77 (s, 1H), 7.70 (dd, J=8.6, 2.6 Hz, 1H), 7.37 (d, J=8.6 Hz, 1H), 7.22-7.11 (m, 3H), 2.97 (t, J=4.7 Hz, 4H), 2.61 (s, 4H), 2.39 (s, 3H). $^{13}$C NMR (101 MHz, Chloroform-d) δ 164.8 (d, J=251.6 Hz), 164.0, 160.1, 158.8, 146.8, 136.9, 133.0 (d, J=3.0 Hz), 129.3 (d, J=8.7 Hz), 128.0 (q, J=28.6 Hz), 125.0, 124.0 (q, J=273.4 Hz), 123.1, 118.0 (q, J=5.8 Hz), 116.1 (d, J=21.8 Hz), 108.5, 55.6, 53.5, 46.2. $^{19}$F NMR (376 MHz, Chloroform-d) δ −60.57, −109.39. MS (ESI) m/z for C$_{22}$H$_{22}$F$_4$N$_5$$^+$ (M+H)$^+$, 432.2 (Calc.), found 432.1; LC-MS purity: 97.09%.

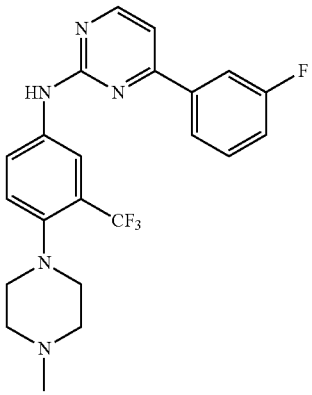

UW110

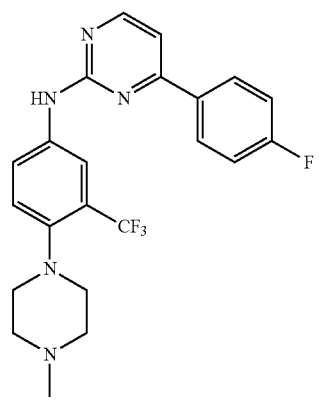

UW109

4-(3-fluorophenyl)-N-(4-(4-methylpiperazin-1-yl)-3-(trifluoromethyl)phenyl)pyrimidin-2-amine (UW110) Method B. The reaction was performed with (E)-3-(dimethylamino)-1-(3-fluorophenyl)prop-2-en-1-one (77 mg, 0.4 mmol), 1-(4-(4-methylpiperazin-1-yl)-3-(trifluoromethyl)phenyl)guanidine (146 mg, 0.48 mmol), K$_2$CO$_3$ (276 mg, 2 mmol) and nBuOH (5 mL). Eluent: 1%-5% MeOH/DCM; yield: 29 mg, 17%; white solid. $^1$H NMR (400 MHz, Chloroform-d) δ 8.50 (d, J=5.3 Hz, 1H), 8.17 (d, J=2.6 Hz, 1H), 7.85 (dd, J=7.9, 1.4 Hz, 1H), 7.79 (dt, J=10.0, 2.2 Hz, 1H), 7.73 (dd, J=8.7, 2.6 Hz, 1H), 7.52-7.43 (m, 2H), 7.40 (d, J=8.7 Hz, 1H), 7.24-7.14 (m, 2H), 2.99 (t, J=4.8 Hz, 4H), 2.64 (s, 4H), 2.41 (s, 3H). $^{13}$C NMR (101 MHz, Chloroform-d) δ 163.8 (d, J=2.6 Hz), 163.4 (d, J=246.4 Hz), 160.1, 159.1, 146.8, 139.3 (d, J=7.6 Hz), 136.8, 130.6 (d, J=8.0 Hz), 128.1 (q, J=28.6 Hz), 125.1, 124.0 (q, J=273.3 Hz), 123.2, 122.8 (d, J=2.9 Hz), 118.0 (q, J=5.6 Hz), 118.0 (d, J=21.2 Hz), 114.2 (d, J=23.1 Hz), 109.0, 55.6, 53.4, 46.1. $^{19}$F NMR (376 MHz, Chloroform-d) δ −60.62, −112.24. MS (ESI) m/z for C$_{22}$H$_{22}$F$_4$N$_5$$^+$ (M+H)$^+$, 432.2 (Calc.), found 432.0; LC-MS purity: 96.67%.

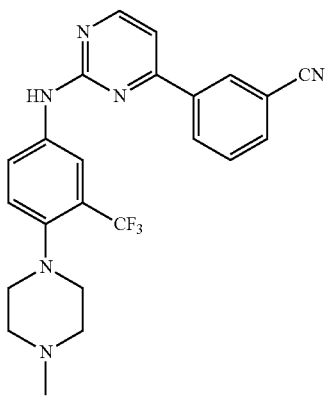

UW111

3-(2-((4-(4-methylpiperazin-1-yl)-3-(trifluoromethyl)phenyl)amino)pyrimidin-4-yl)benzonitrile (UW111) Method B. The reaction was performed with (E)-3-(3-(dimethylamino)acryloyl)benzonitrile (80 mg, 0.4 mmol), 1-(4-(4-methylpiperazin-1-yl)-3-(trifluoromethyl)phenyl)guanidine (146 mg, 0.48 mmol), K$_2$CO$_3$ (276 mg, 2 mmol) and nBuOH (5 mL). Eluent: 1%-5% MeOH/DCM followed by recrystallization with DCM/Hexane; yield: 22 mg, 13%; yellowish solid. NMR (400 MHz, Chloroform-d) δ 8.55 (d, J=5.2 Hz, 1H), 8.36 (t, J=1.7 Hz, 1H), 8.31 (dt, J=8.0, 1.5 Hz, 1H), 8.16 (d, J=2.6 Hz, 1H), 7.78 (dt, J=7.8, 1.4 Hz, 1H), 7.70 (dd, J=8.6, 2.7 Hz, 1H), 7.63 (t, J=7.8 Hz, 1H), 7.54 (s, 1H), 7.40 (d, J=8.7 Hz, 1H), 7.19 (d, J=5.2 Hz, 1H), 2.96 (t, J=4.7 Hz, 4H), 2.59 (s, 4H), 2.37 (s, 3H). $^{13}$C NMR (101 MHz, Chloroform-d) δ 162.7, 160.2, 159.5, 147.3, 138.2, 136.4, 134.1, 131.3, 130.9, 129.9, 128.1 (q, J=28.6 Hz), 125.0, 124.0 (q, J=273.5 Hz), 123.3, 118.4, 118.2 (q, J=5.8 Hz), 113.5, 108.7, 55.6, 53.6, 46.3. $^{19}$F NMR (376 MHz, Chloroform-d) δ -60.58. MS (ESI) m/z for C$_{23}$H$_{22}$F$_3$N$_6^+$ (M+H)$^+$, 439.2 (Calc.), found 439.1; LC-MS purity: 98.84%.

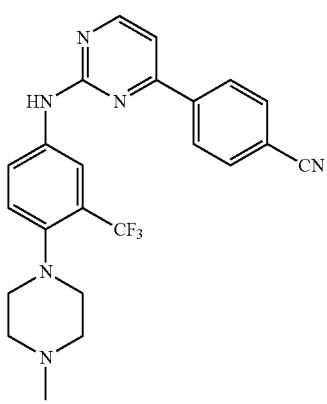

UW112

4-(2-((4-(4-methylpiperazin-1-yl)-3-(trifluoromethyl)phenyl)amino)pyrimidin-4-yl)benzonitrile (UW112) Method B. The reaction was performed with (E)-3-(3-(dimethylamino)acryloyl)benzonitrile (80 mg, 0.4 mmol), 1-(4-(4-methylpiperazin-1-yl)-3-(trifluoromethyl)phenyl)guanidine (146 mg, 0.48 mmol), K$_2$CO$_3$ (276 mg, 2 mmol) and nBuOH (5 mL). Eluent: 1%-5% MeOH/DCM followed by recrystallization with Acetone/Hexane; yield: 13 mg, 8%; yellowish solid. $^1$H NMR (400 MHz, Chloroform-d) δ 8.56 (d, J=5.1 Hz, 1H), 8.26-8.12 (m, 3H), 7.87-7.76 (m, 2H), 7.69 (dd, J=8.6, 2.7 Hz, 1H), 7.49 (s, 1H), 7.40 (d, J=8.6 Hz, 1H), 7.22 (d, J=5.1 Hz, 1H), 2.96 (t, J=4.7 Hz, 4H), 2.59 (s, 4H), 2.38 (s, 3H). $^{13}$C NMR (101 MHz, Chloroform-d) δ 163.0, 160.2, 159.5, 147.3, 141.1, 136.4, 132.8, 128.1 (q, J=28.6 Hz), 127.8, 125.0, 124.0 (q, J=273.5 Hz), 123.3, 118.5, 118.1 (q, J=5.6 Hz), 114.5, 109.2, 55.6, 53.7, 46.3. $^{19}$F NMR (376 MHz, Chloroform-d) δ -60.58. MS (ESI) m/z for C$_{23}$H$_{22}$F$_3$N$_6^+$ (M+H)$^+$, 439.2 (Calc.), found 439.1; LC-MS purity: >99%.

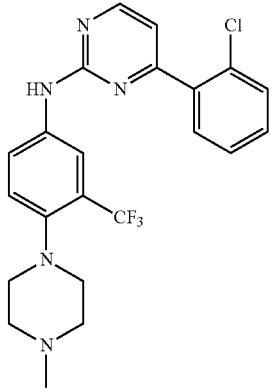

UW113

4-(2-chlorophenyl)-N-(4-(4-methylpiperazin-1-yl)-3-(trifluoromethyl)phenyl)pyrimidin-2-amine (UW113) Method B. The reaction was performed with (E)-1-(2-chlorophenyl)-3-(dimethylamino)prop-2-en-1-one (84 mg, 0.4 mmol), 1-(4-(4-methylpiperazin-1-yl)-3-(trifluoromethyl)phenyl)guanidine (146 mg, 0.48 mmol), K$_2$CO$_3$ (276 mg, 2 mmol) and nBuOH (5 mL). Eluent: 1%-5% MeOH/DCM While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents (including enentiomers) of these exemplary embodiments. All technical publications, patents and published patent applications cited herein are hereby incorporated by reference in their entirety for all purposes.

REFERENCES

1. Mancuso J D, Keep L W. Deployment-related testing and treatment for latent tuberculosis infection, part II. *Mil Med.* 2011; 17610:1088-1092. PMID: 22128639.
2. Caffrey A R, Morrill H J, Puzniak L A, LaPlante K L. Predictors of clinical success among a national Veterans Affairs cohort with methicillin-resistant *Staphylococcus aureus* pneumonia. *Clin Ther.* 2014; 364:552-559. PMID: 24631473.
3. Wlodarchak N, Teachout N, Beczkiewicz J, et al. In Silico Screen and Structural Analysis Identifies Bacterial Kinase Inhibitors which Act with beta-Lactams To Inhibit Mycobacterial Growth. *Mol Pharm.* 2018; 1511:5410-5426. PMID: 30285456.
4. Schaenzer A J, Wlodarchak N, Drewry D H, et al. GW779439X and Its Pyrazolopyridazine Derivatives Inhibit the Serine/Threonine Kinase Stk1 and Act As Antibiotic Adjuvants against beta-Lactam-Resistant *Staphylococcus aureus*. *ACS Infect Dis.* 2018; 410:1508-1518. PMID: 30059625.
5. Beltramini A M, Mukhopadhyay C D, Pancholi V. Modulation of cell wall structure and antimicrobial susceptibility by a *Staphylococcus aureus* eukaryote-like serine/threonine kinase and phosphatase. *Infect Immun.* 2009; 774:1406-1416. PMID: 19188361.
6. O'Neill J. Antimicrobial Resistance: Tackling a crisis for the health and wealth of nations. *Review on Antimicrobial Resistance* 2014.
7. Silver L L. Challenges of antibacterial discovery. *Clin Microbiol Rev.* 2011; 241:71-109. PMID: 21233508.
8. Coates A R, Halls G, Hu Y. Novel classes of antibiotics or more of the same? *Br J Pharmacol.* 2011; 1631:184-194. PMID: 21323894.
9. Boucher H W, Talbot G H, Bradley J S, et al. Bad Bugs, No Drugs: No ESKAPE! An Update from the Infectious Diseases Society of America. *Clinical Infectious Diseases.* 2009; 481:1-12.
10. Seung K J, Keshavjee S, Rich M L. Multidrug-Resistant Tuberculosis and Extensively Drug-Resistant Tuberculosis. *Cold Spring Harb Perspect Med.* 2015; 59:a017863. PMID: 25918181.
11. Velayati A A, Farnia P, Farahbod A M. Overview of drug-resistant tuberculosis worldwide. *Int J Mycobacteriol.* 2016; 5 Suppl 1:S161. PMID: 28043527.
12. Rice L B. Antimicrobial resistance in gram-positive bacteria. *Am J Infect Control.* 2006; 345 Suppl 1:S11-19; discussion S64-73. PMID: 16813977.
13. Filice G A, Nyman J A, Lexau C, et al. Excess costs and utilization associated with methicillin resistance for patients with *Staphylococcus aureus* infection. *Infect Control Hosp Epidemiol.* 2010; 314:365-373. PMID: 20184420.
14. Moran G J, Krishnadasan A, Gorwitz R J, et al. Methicillin-resistant *S. aureus* infections among patients in the emergency department. *N Engl J Med.* 2006; 3557:666-674. PMID: 16914702.
15. Otto M. Basis of virulence in community-associated methicillin-resistant *Staphylococcus aureus*. *Annu Rev Microbiol.* 2010; 64:143-162. PMID: 20825344.
16. Chen C J, Huang Y C. New epidemiology of *Staphylococcus aureus* infection in Asia. *Clin Microbiol Infect.* 2014; 207:605-623. PMID: 24888414.
17. Holmes N E, Johnson P D, Howden B P. Relationship between vancomycin-resistant *Staphylococcus aureus*, vancomycin-intermediate *S. aureus*, high vancomycin MIC, and outcome in serious *S. aureus* infections. *J Clin Microbiol.* 2012; 508:2548-2552. PMID: 22593595.
18. Moravvej Z, Estaji F, Askari E, Solhjou K, Naderi Nasab M, Saadat S. Update on the global number of vancomycin-resistant *Staphylococcus aureus* (VRSA) strains. *Int J Antimicrob Agents.* 2013; 424:370-371. PMID: 23880172.
19. Welte T, Kantecki M, Stone G G, Hammond J. Ceftaroline fosamil as a potential treatment option for *Staphylococcus aureus* community-acquired pneumonia in adults. *Int J Antimicrob Agents.* 2019. PMID: 31404620.
20. Morrisette T, Miller M A, Montague B T, Barber G R, McQueen R B, Krsak M. On- and off-label utilization of dalbavancin and oritavancin for Gram-positive infections. *J Antimicrob Chemother.* 2019; 748:2405-2416. PMID: 31322694.
21. Hasannejad-Bibalan M, Mojtahedi A, Biglari H, Halaji M, Sedigh Ebrahim-Saraie H. Antibacterial Activity of Tedizolid, a Novel Oxazolidinone Against Methicillin-Resistant *Staphylococcus aureus*: A Systematic Review and Meta-Analysis. *Microb Drug Resist.* 2019. PMID: 31290721.
22. Kelley P G, Gao W, Ward P B, Howden B P. Daptomycin non-susceptibility in vancomycin-intermediate *Staphylococcus aureus* (VISA) and heterogeneous-VISA (hVISA): implications for therapy after vancomycin treatment failure. *J Antimicrob Chemother.* 2011; 665:1057-1060. PMID: 21393156.
23. Kourtis A P, Hatfield K, Baggs J, et al. Vital Signs: Epidemiology and Recent Trends in Methicillin-Resistant and in Methicillin-Susceptible *Staphylococcus aureus* Bloodstream Infections—United States. MMWR Morb Mortal Wkly Rep. 2019; 689:214-219. PMID: 30845118.
24. McGrath M, Gey van Pittius N C, van Helden P D, Warren R M, Warner D F. Mutation rate and the emergence of drug resistance in *Mycobacterium tuberculosis*. *J Antimicrob Chemother.* 2014; 692:292-302. PMID: 24072169.
25. Maliwan N, Zvetina J R. Clinical features and follow up of 302 patients with *Mycobacterium kansasii* pulmonary infection: a 50 year experience. *Postgrad Med J.* 2005; 81958:530-533. PMID: 16085747.
26. Achermann Y, Goldstein E J, Coenye T, Shirtliff M E. *Propionibacterium acnes*: from commensal to opportunistic biofilm-associated implant pathogen. *Clin Microbiol Rev.* 2014; 273:419-440. PMID: 24982315.
27. Sewell D L, Coyle M B, Funke G. Prosthetic valve endocarditis caused by *Corynebacterium afermentans* subsp. *lipophilum* (CDC coryneform group ANF-1). *J Clin Microbiol.* 1995; 333:759-761. PMID: 7751392.
28. Wlodarchak N, Xing Y. PP2A as a master regulator of the cell cycle. *Crit Rev Biochem Mol Biol.* 2016; 513:162-184. PMID: 26906453.
29. Patterson H, Nibbs R, McInnes I, Siebert S. Protein kinase inhibitors in the treatment of inflammatory and autoimmune diseases. *Clin Exp Immunol.* 2014; 1761:1-10. PMID: 24313320.
30. Oliveira J, Costa M, de Almeida M S C, da Cruz E S O A B, Henriques A G. Protein Phosphorylation is a Key Mechanism in Alzheimer's Disease. *J Alzheimers Dis.* 2017. PMID: 28527217.
31. Fuller S J, Osborne S A, Leonard S J, et al. Cardiac protein kinases: the cardiomyocyte kinome and differential kinase expression in human failing hearts. *Cardiovasc Res.* 2015; 1081:87-98. PMID: 26260799.
32. Schreiber M, Res I, Matter A. Protein kinases as antibacterial targets. *Curr Opin Cell Biol.* 2009; 212:325-330. PMID: 19246185.
33. Li X, Hou Y, Yue L, Liu S, Du J, Sun S. Potential Targets for Antifungal Drug Discovery Based on Growth and Virulence in Candida albicans. *Antimicrob Agents Chemother.* 2015; 5910:5885-5891. PMID: 26195510.
34. Jacob T, Van den Broeke C, Favoreel H W. Viral serine/threonine protein kinases. *J Virol.* 2011; 853:1158-1173. PMID: 21084474.
35. Naula C, Parsons M, Mottram J C. Protein kinases as drug targets in trypanosomes and Leishmania. *Biochim Biophys Acta.* 2005; 17541-2:151-159. PMID: 16198642.

36. Pensinger D, Schaenzer A, Sauer J-D. Do Shoot the Messenger: PASTA Kinases as Virulence Determinants and Antibiotic Targets. *Trends in Microbiology.* 2017; 00.
37. Ogawara H. Distribution of PASTA domains in penicillin-binding proteins and serine/threonine kinases of Actinobacteria. *J Antibiot* (Tokyo). 2016; 699:660-685. PMID: 26758489.
38. Kusebauch U, Ortega C, Ollodart A, et al. *Mycobacterium tuberculosis* supports protein tyrosine phosphorylation. *Proc Natl Acad Sci USA.* 2014; 11125:9265-9270. PMID: 24927537.
39. Sun F, Ding Y, Ji Q, et al. Protein cysteine phosphorylation of SarA/MgrA family transcriptional regulators mediates bacterial virulence and antibiotic resistance. *Proc Natl Acad Sci USA.* 2012; 10938:15461-15466. PMID: 22927394.
40. Ruggiero A, Squeglia F, Marasco D, Marchetti R, Molinaro A, Berisio R. X-ray structural studies of the entire extracellular region of the serine/threonine kinase PrkC from *Staphylococcus aureus. Biochem J.* 2011; 4351:33-41. PMID: 21208192.
41. Barthe P, Mukamolova G V, Roumestand C, Cohen-Gonsaud M. The structure of PknB extracellular PASTA domain from *Mycobacterium tuberculosis* suggests a ligand-dependent kinase activation. *Structure.* 2010; 185: 606-615. PMID: 20462494.
42. Hardt P, Engels I, Rausch M, et al. The cell wall precursor lipid II acts as a molecular signal for the Ser/Thr kinase PknB of *Staphylococcus aureus. Int J Med Microbiol.* 2017; 3071:1-10. PMID: 27989665.
43. Kaur P, Rausch M, Malakar B, et al. Lipid II interaction with specific residues of *Mycobacterium tuberculosis* PknB extracytoplasmic domain governs its optimal activation. *Nat Commun.* 2019; 101:1231. PMID: 30874556.
44. Shah I M, Laaberki M H, Popham D L, Dworkin J. A eukaryotic-like Ser/Thr kinase signals bacteria to exit dormancy in response to peptidoglycan fragments. *Cell.* 2008; 1353:486-496. PMID: 18984160.
45. Mir M, Asong J, Li X, Cardot J, Boons G J, Husson R N. The extracytoplasmic domain of the *Mycobacterium tuberculosis* Ser/Thr kinase PknB binds specific muropeptides and is required for PknB localization. *PLoS Pathog.* 2011; 77:e1002182. PMID: 21829358.
46. Young T A, Delagoutte B, Endrizzi J A, Falick A M, Alber T. Structure of *Mycobacterium tuberculosis* PknB supports a universal activation mechanism for Ser/Thr protein kinases. *Nat Struct Biol.* 2003; 103:168-174. PMID: 12548283.
47. Lombana T N, Echols N, Good M C, et al. Allosteric activation mechanism of the *Mycobacterium tuberculosis* receptor Ser/Thr protein kinase, PknB. *Structure.* 2010; 1812:1667-1677. PMID: 21134645.
48. Wright D P, Ulijasz A T. Regulation of transcription by eukaryotic-like serine-threonine kinases and phosphatases in Gram-positive bacterial pathogens. *Virulence.* 2014; 58:863-885. PMID: 25603430.
49. Tamber S, Schwartzman J, Cheung A L. Role of PknB kinase in antibiotic resistance and virulence in community-acquired methicillin-resistant *Staphylococcus aureus* strain USA300. *Infect Immun.* 2010; 788:3637-3646. PMID: 20547748.
50. Pensinger D A, Boldon K M, Chen G Y, et al. The *Listeria monocytogenes* PASTA Kinase PrkA and Its Substrate YvcK Are Required for Cell Wall Homeostasis, Metabolism, and Virulence. *PLoS Pathog.* 2016; 1211: e1006001. PMID: 27806131.
51. Bugrysheva J, Froehlich B J, Freiberg J A, Scott J R. Serine/threonine protein kinase Stk is required for virulence, stress response, and penicillin tolerance in *Streptococcus pyogenes. Infect Immun.* 2011; 7910:4201-4209. PMID: 21788381.
52. Kristich C J, Wells C L, Dunny G M. A eukaryotic-type Ser/Thr kinase in *Enterococcus faecalis* mediates antimicrobial resistance and intestinal persistence. *Proc Natl Acad Sci USA.* 2007; 1049:3508-3513. PMID: 17360674.
53. Fernandez P, Saint-Joanis B, Barilone N, et al. The Ser/Thr protein kinase PknB is essential for sustaining mycobacterial growth. *J Bacteriol.* 2006; 18822:7778-7784. PMID: 16980473.
54. Villarino A, Duran R, Wehenkel A, et al. Proteomic identification of *M. tuberculosis* protein kinase substrates: PknB recruits GarA, a FHA domain-containing protein, through activation loop-mediated interactions. *J Mol Biol.* 2005; 3505:953-963. PMID: 15978616.
55. Veyron-Churlet R, Zanella-Cleon I, Cohen-Gonsaud M, Molle V, Kremer L. Phosphorylation of the *Mycobacterium tuberculosis* beta-ketoacyl-acyl carrier protein reductase MabA regulates mycolic acid biosynthesis. *J Biol Chem.* 2010; 28517:12714-12725. PMID: 20178986.
56. Parikh A, Verma S K, Khan S, Prakash B, Nandicoori V K. PknB-mediated phosphorylation of a novel substrate, N-acetylglucosamine-1-phosphate uridyltransferase, modulates its acetyltransferase activity. *J Mol Biol.* 2009; 3862:451-464. PMID: 19121323.
57. Kang C M, Abbott D W, Park S T, Dascher C C, Cantley L C, Husson R N. The *Mycobacterium tuberculosis* serine/threonine kinases PknA and PknB: substrate identification and regulation of cell shape. *Genes Dev.* 2005; 1914:1692-1704. PMID: 15985609.
58. Debarbouille M, Dramsi S, Dussurget O, et al. Characterization of a serine/threonine kinase involved in virulence of *Staphylococcus aureus. J Bacteriol.* 2009; 19113: 4070-4081. PMID: 19395491.
59. Boitel B, Ortiz-Lombardia M, Duran R, et al. PknB kinase activity is regulated by phosphorylation in two Thr residues and dephosphorylation by PstP, the cognate phospho-Ser/Thr phosphatase, in *Mycobacterium tuberculosis. Mol Microbiol.* 2003; 496:1493-1508. PMID: 12950916.
60. Sharma A K, Arora D, Singh L K, et al. Serine/Threonine Protein Phosphatase PstP of *Mycobacterium tuberculosis* Is Necessary for Accurate Cell Division and Survival of Pathogen. *J Biol Chem.* 2016; 29146:24215-24230. PMID: 27758870.
61. Pullen K E, Ng H L, Sung P Y, Good M C, Smith S M, Alber T. An alternate conformation and a third metal in PstP/Ppp, the *M. tuberculosis* PP2C-Family Ser/Thr protein phosphatase. *Structure.* 2004; 1211:1947-1954. PMID: 15530359.
62. Jarick M, Bertsche U, Stahl M, et al. The serine/threonine kinase Stk and the phosphatase Stp regulate cell wall synthesis in *Staphylococcus aureus. Sci Rep.* 2018; 81:13693. PMID: 30209409.
63. Burnside K, Lembo A, de Los Reyes M, et al. Regulation of hemolysin expression and virulence of *Staphylococcus aureus* by a serine/threonine kinase and phosphatase. *PLoS One.* 2010; 56:e11071. PMID: 20552019.
64. Cameron D R, Ward D V, Kostoulias X, et al. Serine/threonine phosphatase Stp1 contributes to reduced susceptibility to vancomycin and virulence in *Staphylococcus aureus. J Infect Dis.* 2012; 20511:1677-1687. PMID: 22492855.

65. Zheng W, Cai X, Xie M, Liang Y, Wang T, Li Z. Structure-Based Identification of a Potent Inhibitor Targeting Stp1-Mediated Virulence Regulation in *Staphylococcus aureus*. *Cell Chem Biol.* 2016; 238:1002-1013. PMID: 27499528.
66. Yang T, Liu T, Gan J, et al. Structural Insight into the Mechanism of *Staphylococcus aureus* Stp1 Phosphatase. *ACS Infect Dis.* 2019; 56:841-850. PMID: 30868877.
67. Wlodarchak N, Guo F, Satyshur K A, et al. Structure of the Ca2+-dependent PP2A heterotrimer and insights into Cdc6 dephosphorylation. *Cell Res.* 2013; 237:931-946. PMID: 23752926.
68. Zhang H, Ericksen S S, Lee C P, et al. Predicting kinase inhibitors using bioactivity matrix derived informer sets. *PLoS Comput Biol.* 2019; 158:e1006813. PMID: 31381559.
69. Jerabek-Willemsen M, André T, Wanner R, et al. MicroScale Thermophoresis: Interaction analysis and beyond. *Journal of Molecular Structure.* 2014; 1077:101-113.
70. Malone C L, Boles B R, Lauderdale K J, Thoendel M, Kavanaugh J S, Horswill A R. Fluorescent Reporters for *Staphylococcus aureus*. *J Microbiol Methods.* 2009; 773: 251-260. PMID: 19264102.
71. Truong-Bolduc Q C, Hooper D C. Phosphorylation of MgrA and its effect on expression of the NorA and NorB efflux pumps of *Staphylococcus aureus*. *J Bacteriol.* 2010; 19210:2525-2534. PMID: 20233929.
72. Crosby H A, Schlievert P M, Merriman J A, King J M, Salgado-Pabon W, Horswill A R. The *Staphylococcus aureus* Global Regulator MgrA Modulates Clumping and Virulence by Controlling Surface Protein Expression. *PLoS Pathog.* 2016; 125:e1005604. PMID: 27144398.
73. Glanzmann P, Gustafson J, Komatsuzawa H, Ohta K, Berger-Bachi B. glmM operon and methicillin-resistant glmM suppressor mutants in *Staphylococcus aureus*. *Antimicrob Agents Chemother.* 1999; 432:240-245. PMID: 9925512.
74. Luft J R, Collins R J, Fehrman N A, Lauricella A M, Veatch C K, DeTitta G T. A deliberate approach to screening for initial crystallization conditions of biological macromolecules. *J Struct Biol.* 2003; 1421:170-179. PMID: 12718929.
75. Lipinski C A, Lombardo F, Dominy B W, Feeney P J. Experimental and computational approaches to estimate solubility and permeability in drug discovery and development settings. *Adv Drug Deliv Rev.* 1997; 23:3-26. PMID: 11259830.
76. Mugumbate G, Overington J P. The relationship between target-class and the physicochemical properties of antibacterial drugs. *Bioorg Med Chem.* 2015; 2316:5218-5224. PMID: 25975639.
77. Chapman T M, Bouloc N, Buxton R S, et al. Substituted aminopyrimidine protein kinase B (PknB) inhibitors show activity against *Mycobacterium tuberculosis*. *Bioorg Med Chem Lett.* 2012; 229:3349-3353. PMID: 22469702.
78. Sipos A, Pato J, Szekely R, et al. Lead selection and characterization of antitubercular compounds using the Nested Chemical Library. *Tuberculosis (Edinb).* 2015; 95 Suppl 1:S200-206. PMID: 25801335.
79. Wang T, Bemis G, Hanzelka B, et al. Mtb PKNA/PKNB Dual Inhibition Provides Selectivity Advantages for Inhibitor Design To Minimize Host Kinase Interactions. *ACS Med Chem Lett.* 2017; 812:1224-1229. PMID: 29259738.
80. Lougheed K E, Osborne S A, Saxty B, et al. Effective inhibitors of the essential kinase PknB and their potential as anti-mycobacterial agents. *Tuberculosis (Edinb).* 2011; 914:277-286. PMID: 21482481.
81. Schaenzer A J, Wlodarchak N, Drewry D H, et al. A screen for kinase inhibitors identifies antimicrobial imidazopyridine aminofurazans as specific inhibitors of the *Listeria monocytogenes* PASTA kinase PrkA. *J Biol Chem.* 2017; 29241:17037-17045. PMID: 28821610.
82. Stevens K L, Reno M J, Alberti J B, et al. Synthesis and evaluation of pyrazolo[1,5-b]pyridazines as selective cyclin dependent kinase inhibitors. *Bioorg Med Chem Lett.* 2008; 1821:5758-5762. PMID: 18835709.
83. Fabbro D, Ruetz S, Buchdunger E, et al. Protein kinases as targets for anticancer agents: from inhibitors to useful drugs. *Pharmacol Ther.* 2002; 932-3:79-98. PMID: 12191602.
84. Basell K, Otto A, Junker S, et al. The phosphoproteome and its physiological dynamics in *Staphylococcus aureus*. *Int J Med Microbiol.* 2014; 3042:121-132. PMID: 24457182.
85. Salinas G, Gao W, Wang Y, et al. The Enzymatic and Structural Basis for Inhibition of *Echinococcus granulosus* Thioredoxin Glutathione Reductase by Gold(I). *Antioxid Redox Signal.* 2017; 2718:1491-1504. PMID: 28463568.
86. Michalik S, Depke M, Murr A, et al. A global *Staphylococcus aureus* proteome resource applied to the in vivo characterization of host-pathogen interactions. *Sci Rep.* 2017; 71:9718. PMID: 28887440.
87. Fey P D, Endres J L, Yajjala V K, et al. A genetic resource for rapid and comprehensive phenotype screening of nonessential *Staphylococcus aureus* genes. *MBio.* 2013; 41:e00537-00512. PMID: 23404398.
88. Muller M, Reiss S, Schluter R, et al. Deletion of membrane-associated Asp23 leads to upregulation of cell wall stress genes in *Staphylococcus aureus*. *Mol Microbiol.* 2014; 936:1259-1268. PMID: 25074408.

What is claimed is:

1. A compound for selectively inhibiting a protein kinase in a bacterium of a human subject, the compound having the chemical structure:

wherein:

$R_1$=Me, Et, n-Pr, —$CH_2CH_2OH$, —$CH_2CH_2OP(O)(OH)_2$, or —$CH_2CH_2NMe_2$;

$R_2$=H, Me, Et, o-Pr, i-Pr, $CF_3$, Cl, or OMe;

$R_3$=H, Me, NHMe, NHBn, Cl, $NO_2$OMe, F, or CN; and wherein said chemical structure is capable of inhibiting a Penicillin-binding And Serine/Threonine Associated (PASTA) kinase in the human subject and wherein the compound has any one of the following chemical structures:

31
-continued

32
-continued

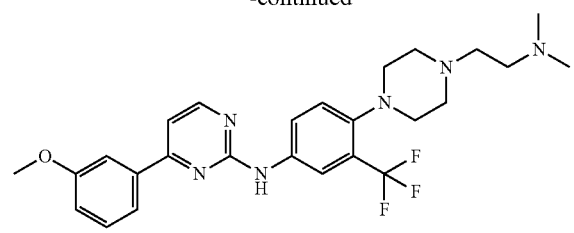
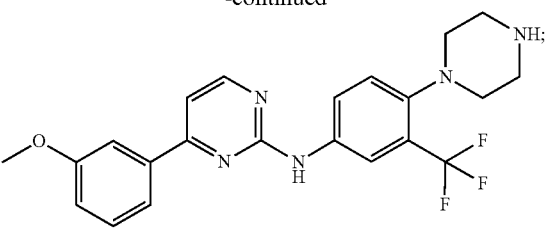
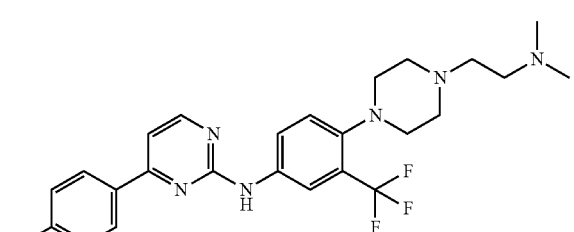
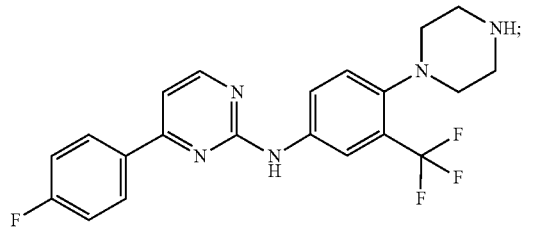
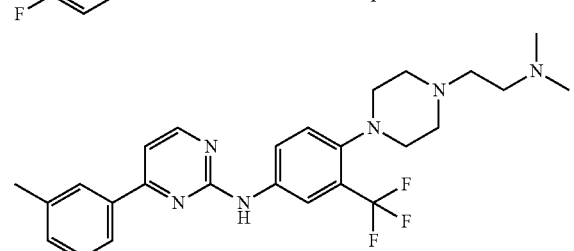
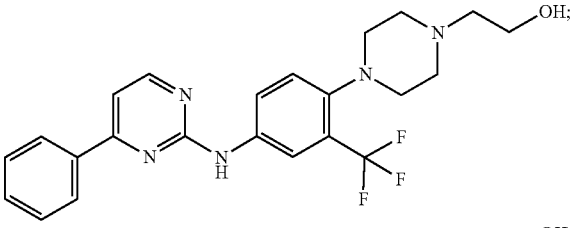
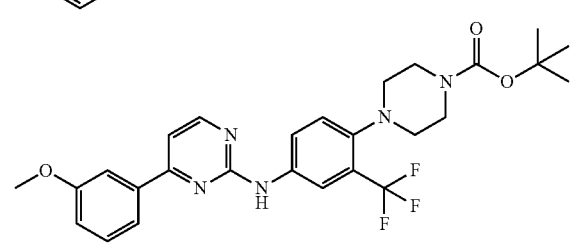
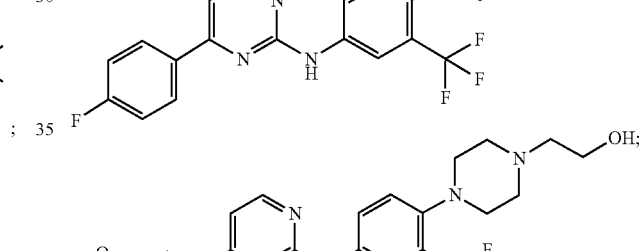
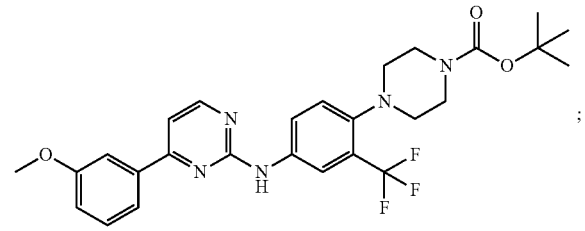
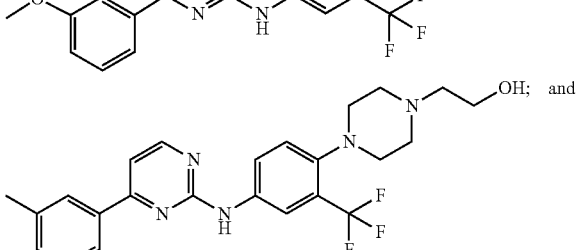
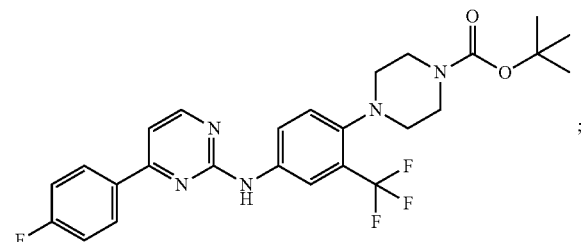
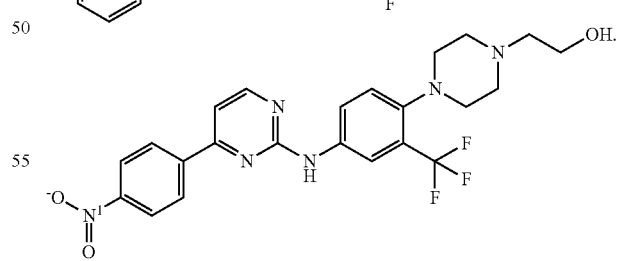
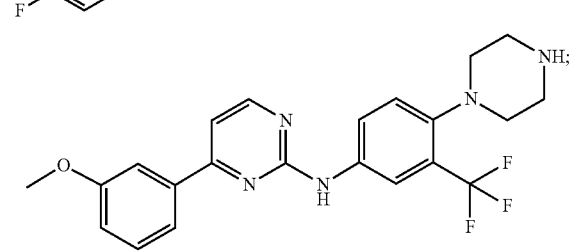
2. The compound according to claim 1, wherein said inhibited PASTA kinase is PknB.
3. A method of inhibiting a protein kinase in a subject, comprising
administering to said subject an effective amount of a compound according to claim 1, and
inhibiting the protein kinase in said subject.

4. The method of claim 3, further comprising the step of inhibiting a Penicillin-binding And Serine/Threonine Associated (PASTA) kinase in said subject.

5. The method of claim 4, wherein said PASTA kinase is PknB.

6. A method of treating a bacterial infection in a subject, comprising
administering an effective amount of a compound according to claim 1; and
treating the bacterial infection in said subject.

7. The method of claim 6, wherein the bacterial infection comprises a *Mycobacterium tuberculosis* infection.

8. The method of claim 6, further comprising the step of inhibiting a Penicillin-binding And Serine/Threonine Associated (PASTA) kinase.

9. The method of claim 8, wherein said PASTA kinase is PknB.

10. The method of claim 6, further comprising the step of administering a β-lactam antibiotic to the subject.

11. A method of treating a bacterial infection in a subject, comprising
co-administering an effective amount of a compound according to claim 1 and an effective amount of an antibiotic; and
treating the bacterial infection in said subject.

12. The method of claim 11, wherein the antibiotic is a beta-lactam antibiotic.

13. The compound according to claim 1, wherein the compound has one of the following chemical structures:

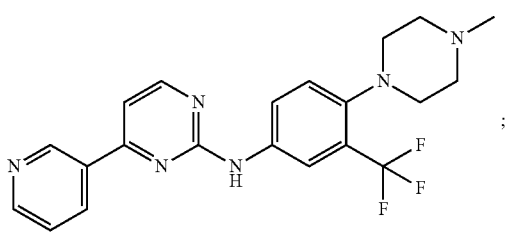

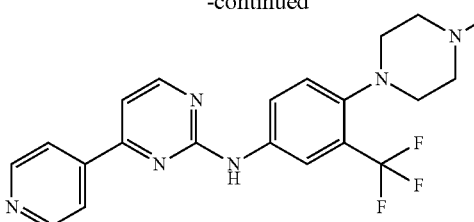

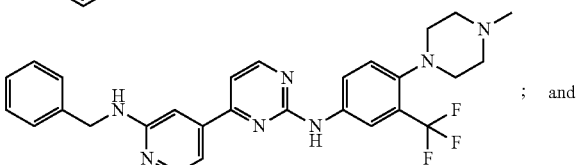

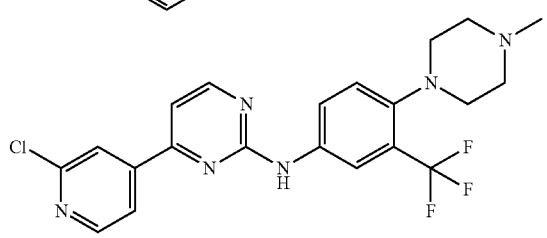

14. The compound according to claim 13, wherein the compound has the following chemical structure:

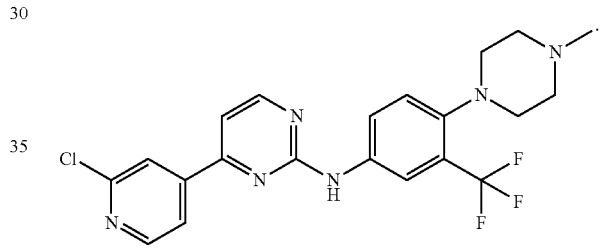

* * * * *